(12) United States Patent
Ivashin et al.

(10) Patent No.: US 9,395,333 B2
(45) Date of Patent: Jul. 19, 2016

(54) ION MOBILITY SPECTROMETER DEVICE WITH EMBEDDED FAIMS

(75) Inventors: Dmitriy V. Ivashin, Peabody, MA (US); Saïd Boumsellek, San Diego, CA (US)

(73) Assignee: Implant Sciences Corporation, Wilmington, MA (US)

( * ) Notice: Subject to any disclaimer, the term of this patent is extended or adjusted under 35 U.S.C. 154(b) by 667 days.

(21) Appl. No.: 13/506,120

(22) Filed: Mar. 28, 2012

(65) Prior Publication Data
US 2012/0326020 A1  Dec. 27, 2012

Related U.S. Application Data

(60) Provisional application No. 61/499,820, filed on Jun. 22, 2011.

(51) Int. Cl.
*G01N 27/62* (2006.01)

(52) U.S. Cl.
CPC ............ *G01N 27/624* (2013.01); *G01N 27/622* (2013.01)

(58) Field of Classification Search
CPC ........................... G01N 27/622; G01N 27/624
USPC ....................................................... 250/290
See application file for complete search history.

(56) References Cited

U.S. PATENT DOCUMENTS

| | | | |
|---|---|---|---|
| 5,420,424 A | 5/1995 | Carnahan et al. | |
| 5,801,379 A | 9/1998 | Kouznetsov | |
| 6,809,313 B1 | 10/2004 | Gresham et al. | |
| 7,119,328 B2 | 10/2006 | Kaufman et al. | |
| 7,223,967 B2 | 5/2007 | Guevremont et al. | |
| 7,368,709 B2 | 5/2008 | Guevremont | |
| 7,399,958 B2 | 7/2008 | Miller et al. | |
| 7,714,284 B2 | 5/2010 | Miller et al. | |
| 7,838,823 B1 | 11/2010 | Pfiefer et al. | |
| 8,173,959 B1 * | 5/2012 | Boumsellek | G01N 27/622 250/281 |
| 9,006,678 B2 * | 4/2015 | Ivashin | H01J 31/04 250/423 R |
| 9,068,943 B2 * | 6/2015 | Ivashin | H01J 49/0036 |

(Continued)

FOREIGN PATENT DOCUMENTS

SU        1337934 A2    9/1987

OTHER PUBLICATIONS

A.D. Appelhans and D.A. Dahl, "Simion ion optics simulation at atmospheric pressure," *Int. J. Mass. Spectrom*, 244 (2005), pp. 1-14.

(Continued)

*Primary Examiner* — Robert Kim
*Assistant Examiner* — J Choi
(74) *Attorney, Agent, or Firm* — Muirhead and Saturnelli, LLC

(57) ABSTRACT

A tandem instrument using a variable frequency pulsed ionization source and two separation techniques, low (IMS) and high (FAIMS) field mobility is provided. The analytical stage features a field driven FAIMS cell embedded on-axis within the IMS drift tube. The FAIMS cell includes two parallel grids of approximately the same diameter as the IMS rings and can be placed anywhere along the drift tube and biased according to their location in the voltage divider ladder to create the same IMS field. The spacing between the grids constitutes the analytical gap where ions are subject, in addition to the drift field, to the asymmetric dispersive field of the FAIMS. The oscillatory motion performed during the high and low voltages of the asymmetric waveform separates the ions according to the difference in their mobilities.

15 Claims, 19 Drawing Sheets

(56) References Cited

U.S. PATENT DOCUMENTS

| | | | |
|---|---|---|---|
| 9,070,542 B2* | 6/2015 | Ivashin | H01J 49/105 |
| 9,267,920 B2* | 2/2016 | Anderson | G01N 27/622 |
| 2003/0038235 A1 | 2/2003 | Guevremont et al. | |
| 2003/0089847 A1* | 5/2003 | Guevremont et al. | 250/282 |
| 2005/0051719 A1 | 3/2005 | Miller et al. | |
| 2005/0109930 A1 | 5/2005 | Hill et al. | |
| 2007/0176092 A1 | 8/2007 | Miller et al. | |
| 2008/0073502 A1 | 3/2008 | Schneider et al. | |
| 2008/0142700 A1 | 6/2008 | Dahl et al. | |
| 2008/0179515 A1 | 7/2008 | Sperline | |
| 2008/0237458 A1 | 10/2008 | Wang | |
| 2009/0278040 A1 | 11/2009 | Wu | |
| 2010/0207022 A1* | 8/2010 | Tang et al. | 250/282 |
| 2011/0133076 A1 | 6/2011 | Miller et al. | |
| 2011/0260053 A1 | 10/2011 | Atkinson et al. | |
| 2012/0273669 A1* | 11/2012 | Ivashin et al. | 250/282 |
| 2015/0233866 A1* | 8/2015 | Verenchikov | G01N 27/622 250/282 |
| 2015/0323500 A1* | 11/2015 | Davis | G01N 27/624 250/281 |

OTHER PUBLICATIONS

I. A. Buryakov et al., "A new method of separation of multi-atomic ions by mobility at atmospheric pressure using a high-frequency amplitude-asymmetric strong electric field," International Journal of Mass Spectrometry and Ion Processes, vol. 128, Issue 3, Oct. 9, 1993, pp. 143-148.

U.S. Appl. No. 11/941,939, filed Nov. 17, 2007, Boumsellek et al.

U.S. Appl. No. 13/066,894, filed Apr. 27, 2011, Ivashin et al.

M. J. Pollard et al., "Ion mobility spectrometer: field asymmetric ion mobility spectrometer-mass spectrometry," Int. J. Ion Mobil. Spec., Springer-Verlag, Mar. 9, 2011, 8 pp.

A. A. Shvartsburg et al., "Optimization of the Design and Operation of FAIMS Analyzers," J. Am. Soc. Mass. Spectrom. 2005, 16, Nov. 23, 2004, pp. 2-12.

E. V. Krylov, "Pulses of Special Shapes Formed on a Capacitive Load," Instruments and Experimental Techniques, vol. 40, No. 5, 1997, pp. 628-631.

E. V. Krylov, et al., "Selection and generation of waveforms for differential mobility spectrometry," Review of Scientific Instruments, 81, 024101 (2010), 11 pp.

R. Guevremont, "High-Field Asymmetric Waveform Ion Mobility Spectrometry (FAIMS)," Canadian Journal of Analytical Sciences and Spectroscopy, vol. 49, No. 3, 2004, pp. 105-113.

"Application Circuits of Switch Mode Power Transformers," Butler Winding, retrieved from <<http://www.butlerwinding.com>> on Nov. 8, 2010, 3 pp.

Pollard, Matthew J., et al., "Ion mobility spectrometer—field asymmetric ion mobility spectrometer—mass spectrometry", International Journal for Ion Mobility Spectrometry, vol. 14, No. 1, Mar. 9, 2011, XP55028073, ISSN: 1435-6163.

Tang, Keqi, et al., "Two-Dimensional Gas-Phase Separations Coupled to Mass Spectrometry for Analysis of Complex Mixtures", Analytical Chemistry, vol. 77, No. 19, Oct. 1, 2005, XP55007024, ISSN: 0003-2700.

* cited by examiner

400

1090

ION MOBILITY SPECTROMETER DEVICE WITH EMBEDDED FAIMS

RELATED APPLICATIONS

This application claims priority to U.S. Provisional App. No. 61/499,820, filed Jun. 22, 2011, which is incorporated herein by reference.

TECHNICAL FIELD

This application is related to the field of chemical analysis and, in particular, ion mobility spectrometry.

BACKGROUND OF THE INVENTION

In field applications, chemical analysis instruments may be confronted with various complex mixtures regardless of indoor or outdoor environments. Such mixtures may cause instrument contamination and confusion due to the presence of molecular interferents producing signatures that are either identical to that of the chemical compounds of interest or unresolved by the analytical instrument due to its limited resolution. An interferent can also manifest its presence by affecting the limit of detection of the compound of interest. A multi-stage analysis approach may therefore be used to reduce the chemical noise and produce enough separation for deterministic detection and identification. The multi-stage analysis may include either a single separation technique such as mass spectrometry (MS) in $MS^n$ instruments or a combination of different separation techniques. These are called orthogonal techniques since, even though they may operate in tandem, they measure different properties of the same molecule by producing multi-dimensional spectra hence increasing the probability of detection and accuracy of detection. For field instruments, such techniques may be physically and operationally integrated in order to produce complementary information hence improving overall selectivity without sacrificing speed and sensitivity.

In the area of trace explosives detection, ion mobility spectrometry may be commonly used at passenger checkpoints in airports. The technique relies on the availability of sufficient explosives residue (particles and/or vapor) on the passenger skin, clothing, and personnel items to signal a threat. The assumption being that due to their high sticking coefficient it is difficult to avoid contamination by explosives particles during the process of handling a bomb. The same high sticking coefficient results in extremely low vapor pressures and hence makes their detection difficult. The acquisition of vapor and/or particle samples may be achieved by either swiping "suspect" surfaces of luggage or persons, or in the case of portals and/or by sending pulses of compressed air intended to liberate particles off the person's clothing, skin, shoes etc. . . . In both cases the sample is introduced into an ion mobility spectrometer (IMS) for analysis.

Ion mobility spectrometry utilizes relatively low electric fields to propel ions through a drift gas chamber and separate these ions according to their drift velocity. In IMS, the ion drift velocity is proportional to the field strength at low electric fields (~200 V/cm), and thus an ion's mobility (K) is independent of the applied field. In the IMS both analyte and background molecules are typically ionized using radioactive alpha or beta emitters and the ions are injected into a drift tube with a constant low electric field (300 V/cm or less) where they are separated on the basis of their drift velocity and hence their mobility. The mobility is governed by the ion collisions with the drift gas molecules flowing in the opposite direction. The ion-molecule collision cross section depends on the size, the shape, the charge, and the mass of the ion relative to the mass of the drift gas molecule. The resulting chromatogram is compared to a library of known patterns to identify the substance collected. Since the collision cross section depends on more than one ion characteristic, peak identification is not unique. IMS systems measure a secondary and less specific property of the target molecule—the time it takes for the ionized molecule to drift through a tube filled with a viscous gas under an electric field—and the identity of the molecule is inferred from the intensity vs time spectrum. Since different molecules may have similar drift times, IMS inherently has limited chemical specificity and therefore is vulnerable to interfering molecules.

High-field asymmetric waveform ion mobility spectrometry (FAIMS) is an emerging detection technology which can operate at atmospheric pressure to separate and detect ions, as first described in detail by Buryakov, I. A.; Krylov, E. V.; Nazarov, E. G.; Rasulev, U. K., *International Journal of Mass Spectrometry and Ion Processes* 1993, 128 (3), pp. 143-148, which is incorporated herein by reference. FAIMS separates ions by utilizing the mobility differences of ions at high and low fields. Compared to conventional ion mobility, FAIMS operates at much higher fields (~10,000 V/cm) where ion mobilities become dependent on the applied field and are better represented by $K_h$, a non-constant high-field mobility term. Variations in $K_h$ from the low-field K, and the compound-dependence of that variation aids FAIMS in its separation power. FAIMS utilizes a combination of alternating current (AC) and direct current (DC) voltages to transmit ions of interest and filter out other ions, thus improving specificity, and decreasing the chemical noise. FAIMS can reduce false positives, since two different compounds having the same low-field mobility can often be distinguished in a high-field environment.

Ions are separated in FAIMS by their difference in mobility at high ($K_h$) and at low (K) electric fields. At a constant gas number density, N, the non-linear dependence of an ion's mobility in high electric fields can be described by $$K_h(E) = K_0[1 + \alpha(E/N)^2 + \beta(E/N)^4 + \ldots] \qquad \text{Eq. (1)}$$

where $K_0$ is the ion mobility coefficient at zero electric field and $\alpha$ and $\beta$ describe the dependence of the ion's mobility at a high electric field in a particular drift gas. Equation 1 is an infinite series, but at realistic field intensities the terms above the $4^{th}$ order become insignificant. FAIMS cells are commonly comprised of two parallel electrodes, one typically held at a ground potential while the other has an asymmetric waveform applied to it. A commonly used asymmetric waveform, described by V(t) in Equation 2, includes a high-voltage component (also referred to as $V_1$ or dispersion voltage [DV]) which lasts for a short period of time ($t_1$) relative to a longer lasting ($t_2$) low-voltage component ($V_2$) of opposite polarity. Most FAIMS work up to date has employed a sinusoidal wave, plus its first harmonic at twice the frequency, as shown in Equation 2, where $\omega$ is the frequency in radians per second.

$$V(t) = (0.61) V_1 \sin(\omega t) + (0.39) V_1 \sin(2\omega t - \pi/2) \qquad \text{Eq. (2)}$$

The waveform is constructed so that the voltage-time product applied to the electrode is equal to zero, as displayed in Equation 3.

$$V_1 t_1 + V_2 t_2 = 0 \qquad \text{Eq. (3)}$$

At high electric fields, the application of this waveform will cause an ion to experience a net drift toward one of the electrodes. Ions passing between the electrodes encounter this displacement because the ion's mobility during the high-voltage component ($K_h$) is different than that from the low-voltage mobility (K). In other words, the ion will move a different distance during the high-voltage portion than during the low-voltage portion. This ion will continue to migrate towards one of the electrodes and subsequently be lost unless a DC compensation voltage (CV) is applied to offset the drift. The CV values required to offset the drift of different ions will be different if the $K_h$/K ratio of the ions are different. Thus, a mixture of compounds can be successfully separated by scanning the CV, allowing each compound to transmit at its characteristic CV, creating a CV spectrum.

When higher electric fields are applied to the FAIMS electrodes, an ion can have three possible changes in ion mobility. The mobility of type A ions increases with increasing electric field strength, the mobility of type C ions decreases, and the mobility of type B ions increases initially before decreasing at yet higher fields. Most low-mass ions (<m/z 300) are type A ions, whereas most high-mass ions are type C ions.

In addition to stand-alone use, FAIMS devices may be used to filter ions prior to analyses with mass spectrometry (MS) devices and/or drift tube IMS devices, and reference is made, for example, to U.S. Patent App. Publication No. 2010/0207022 A1 to Tang et al, published Aug. 19, 2010, entitled *"Platform for Field Asymmetric Waveform Ion Mobility Spectrometry with Ion Propulsion Modes Employing Gas Flow and Electric Field,"* which is incorporated herein by reference. Tang et al. principally discuss multiple device instruments stages using a FAIMS device coupled to a subsequent device, such as an IMS or MS device, and in which the FAIMS device may be rapidly switched on or off to enable more sensitive analyses using the other stage(s). Paragraph [0010] of Tang et al. suggests that in such multiple device instrument stages it is possible for the other stage(s) to precede the FAIMS device; however, this discussion in Tang et al. is still directed towards the goal of providing a method for effective, rapid and convenient switch-off of the FAIMS separation in hybrid platforms to enable more sensitive analyses using the other stage(s).

Accordingly, it would be desirable to provide a system that provides for flexible operation to handle a variety of detection scenarios and that provides for enhanced chemical detection and identification capabilities.

SUMMARY OF THE INVENTION

According to the system described herein, a chemical detection and analysis system may include an ion mobility spectrometer (IMS) device having a drift tube that includes a first end with a sample inlet and a second end that is downstream from the first end. Ions from ionization of a sample input via the sample inlet may be introduced into the drift tube and are propelled through the drift tube in a direction along an axis of the drift tube. A high field asymmetric waveform ion mobility spectrometer (FAIMS) device may be embedded along the axis of the drift tube of the EMS device, wherein the FAIMS device causes oscillations of the ions in the direction along the axis of the drift tube resulting in a net change in velocity of at least some of the ions moving in the direction along the axis of the drift tube. The FAIMS device may have a planar geometry and/or a non-planar geometry and/or may be field-driven. The drift tube may include electrodes that propel the ions through the drift tube in the direction of the axis of the drift tube and propel the ions through the FAIMS cell in the direction of the axis of the drift tube. A collector may be provided that analyzes ions of interest from the FAIMS device, and an aperture grid may be provided that directs the ions of interest to the collector. A controller may be provided that controls a field generated in the FAIMS device to cause the oscillations of the ions. The FAIMS device may be a first FAIMS device and the system may further include a second FAIMS device embedded along the axis of the drift tube of the IMS device.

According further to the system described herein, a method for performing chemical detection and analysis includes ionizing a sample in an ion mobility spectrometer (IMS) device having a drift tube that includes a first end with a sample inlet and a second end that is downstream from the first end. Ions from the ionization of the sample may be introduced into the drift tube and are propelled through the drift tube in a direction along an axis of the drift tube. A high field asymmetric waveform ion mobility spectrometer (FAIMS) device embedded along the axis of the drift tube of the IMS device may be controlled. The FAIMS device may be controlled to cause oscillations of the ions in the direction along the axis of the drift tube resulting in a net change in velocity of at least some of the ions moving in the direction along the axis of the drift tube. The FAIMS device may have a planar geometry and/or a non-planar geometry and/or may be field-driven. The drift tube may include electrodes that propel the ions through the drift tube in the direction of the axis of the drift tube and propel the ions through the FAIMS cell in the direction of the axis of the drift tube. The method may further include directing the ions of interest to a collector and analyzing the ions of interest at the collector. The method may further include controlling a field generated in the FAIMS device to cause the oscillations of the ions. The FAIMS device may be a first FAIMS device, and the method may further include controlling a second FAIMS device embedded along the axis of the drift tube of the IMS device, wherein the second FAIMS device is controlled to cause oscillations of the ions in the direction along the axis of the drift tube resulting in a net change in velocity of at least some of the ions moving in the direction along the axis of the drift tube.

According further to the system described herein, a non-transitory computer readable to medium method stores software for performing chemical detection and analysis. The software may include executable code that controls ionizing of a sample in an ion mobility spectrometer (IMS) device having a drift tube that includes a first end with a sample inlet and a second end that is downstream from the first end, wherein ions from the ionization of the sample are introduced into the drift tube and are propelled through the drift tube in a direction along an axis of the drift tube. Executable code may be provided that controls a high field asymmetric waveform ion mobility spectrometer (FAIMS) device embedded along the axis of the drift tube of the IMS device, wherein the FAIMS device is controlled to cause oscillations of the ions in the direction along the axis of the drift tube resulting in a net change in velocity of at least some of the ions moving in the direction along the axis of the drift tube. The FAIMS device may have a planar geometry and/or a non-planar geometry and/or may be field-driven. The drift tube may include electrodes that propel the ions through the drift tube in the direction of the axis of the drift tube and propel the ions through the FAIMS cell in the direction of the axis of the drift tube. Executable code may be provided that controls directing of the ions of interest to a collector and analyzing the ions of interest at the collector. Executable code may be provided that controls a field generated in the FAIMS device to cause the oscillations of the ions. The FAIMS device may be a first FAIMS device, and the software may further include executable code that controls a second FAIMS device embedded along the axis of the drift tube of the IMS device, wherein the second FAIMS device is controlled to cause oscillations of the ions in the direction along the axis of the drift tube resulting in a net change in velocity of at least some of the ions moving in the direction along the axis of the drift tube.

BRIEF DESCRIPTION OF THE DRAWINGS

Embodiments of the system described herein are explained with reference to the several figures of the drawings, which are briefly described as follows.

DETAILED DESCRIPTION OF VARIOUS EMBODIMENTS

The system described herein provides for use of combined techniques, such as low (IMS) and high (FAIMS) field mobility techniques, to offer several advantages including low cost, no vacuum required, and the generation of 2-D spectra for enhanced detection and identification. Operation of the two analytical devices may provide a system with advantageous flexibility by allowing adaptation of the hyphenated instrument to the application's requirements. With the IMS-FAIMS hardware level flexibility, the instruments may be configured and optimized to exploit different trade-offs suitable for a variety of detection scenarios for different lists of target compounds. In various embodiments discussed herein, the IMS and FAIMS devices may be orthogonal to each other, specifically in which the flow directions of ions in the IMS and FAIMS devices are orthogonal. In other embodiments discussed in detail herein, the FAIMS device may be embedded in the IMS device and in which the flow directions of ions may be co-axial along the IMS and FAIMS devices.

Figure 1A:
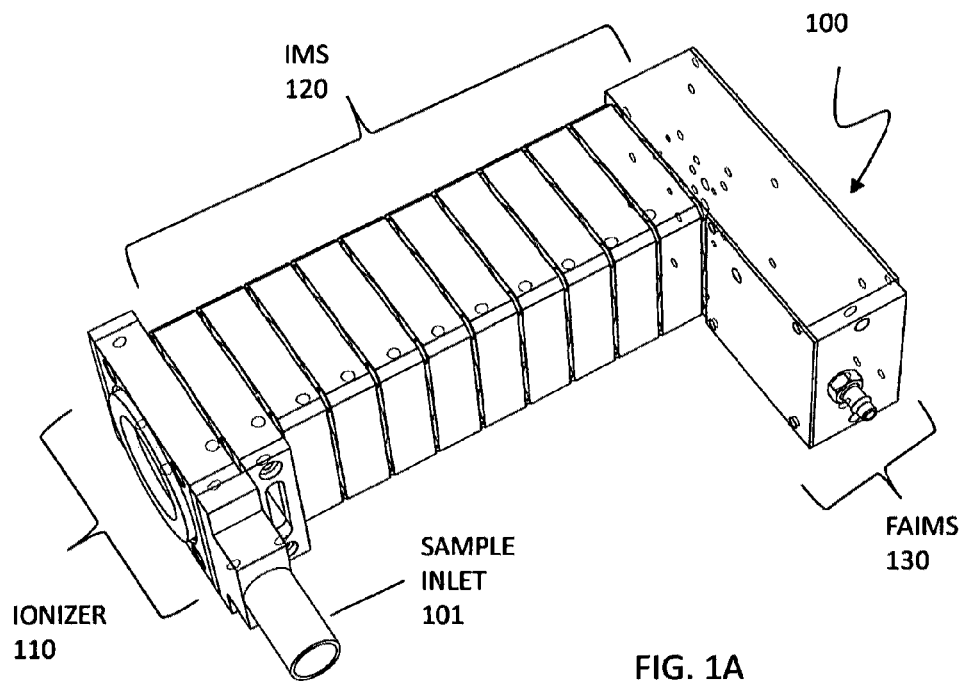
FIGS. 1A and 1B are schematic illustrations of a system that includes interfacing IMS and FAIMS devices according to an embodiment of the system described herein.
Figure 1B:
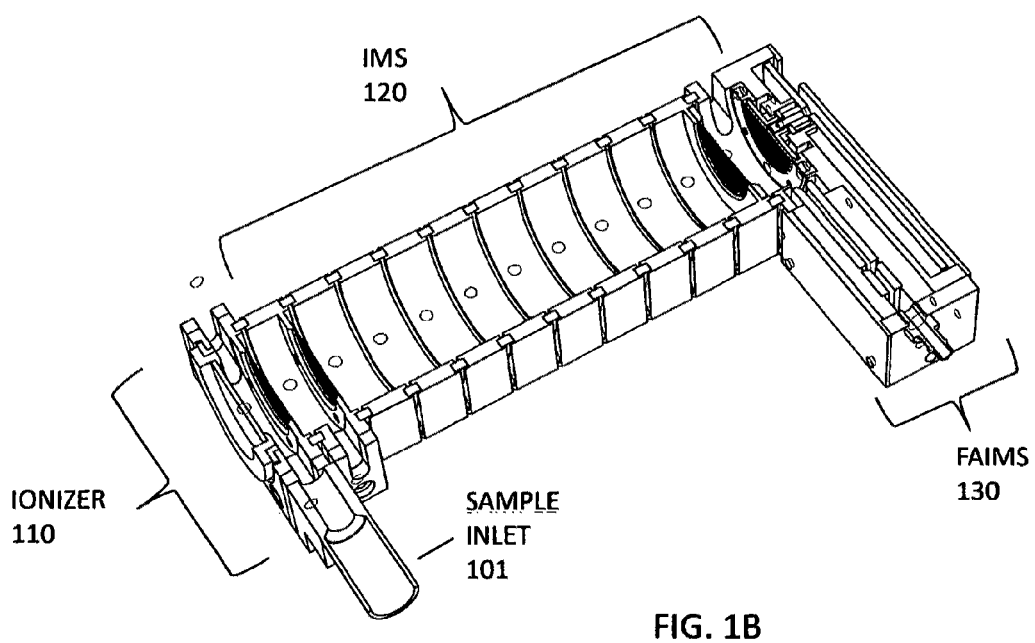

FIGS. 1A and 1B are schematic illustrations of a system 100 that includes interfacing IMS and FAIMS devices according to an embodiment of the system described herein. FIG. 1A is a schematic view of the system 100 and FIG. 1B shows a cross-sectional view. The system 100 may be used to generate two dimensional data sets including drift time chromatograms and compensation voltage spectra. The system 100 may include an ionizer/ion source 110, a IMS device 120 including a drift tube, and an FAIMS device 130 (single and/or array of devices) placed at a 90 degree angle at the IMS drift tube device 120. The ionizer/ion source 110 may provide a continuous or a pulsed ion current depending on an operational mode. In an embodiment, the ionizer/ion source 110 may include a pulsed ion source, such as a spark ion source, that may send either individual packets of ions or a continuous flow of ions by varying the frequency. Additionally or alternatively, a continuous ion source may be used including a DC corona or a radioactive source via an ion gate placed at the entrance of the IMS drift tube 120. In an embodiment, the IMS drift tube device 120 may be manufactured by Implant Sciences of Wilmington, MA. The IMS device 120 and the FAIMS device 130 may be independent and their respective electrometer circuits may be mounted on the same printed circuit board for optimum integration. In this configuration the IMS 120 may be used as a front-end filter for the FAIMS 130. Such a configuration may accomplish at least two goals: (1) pre-separation of target analytes and (2) only ions are injected into the FAIMS gas flow and driven by the gas flow into the analytical gap of the FAIMS device 130, hence keeping it free of moisture and other contaminants.

Figure 2A:
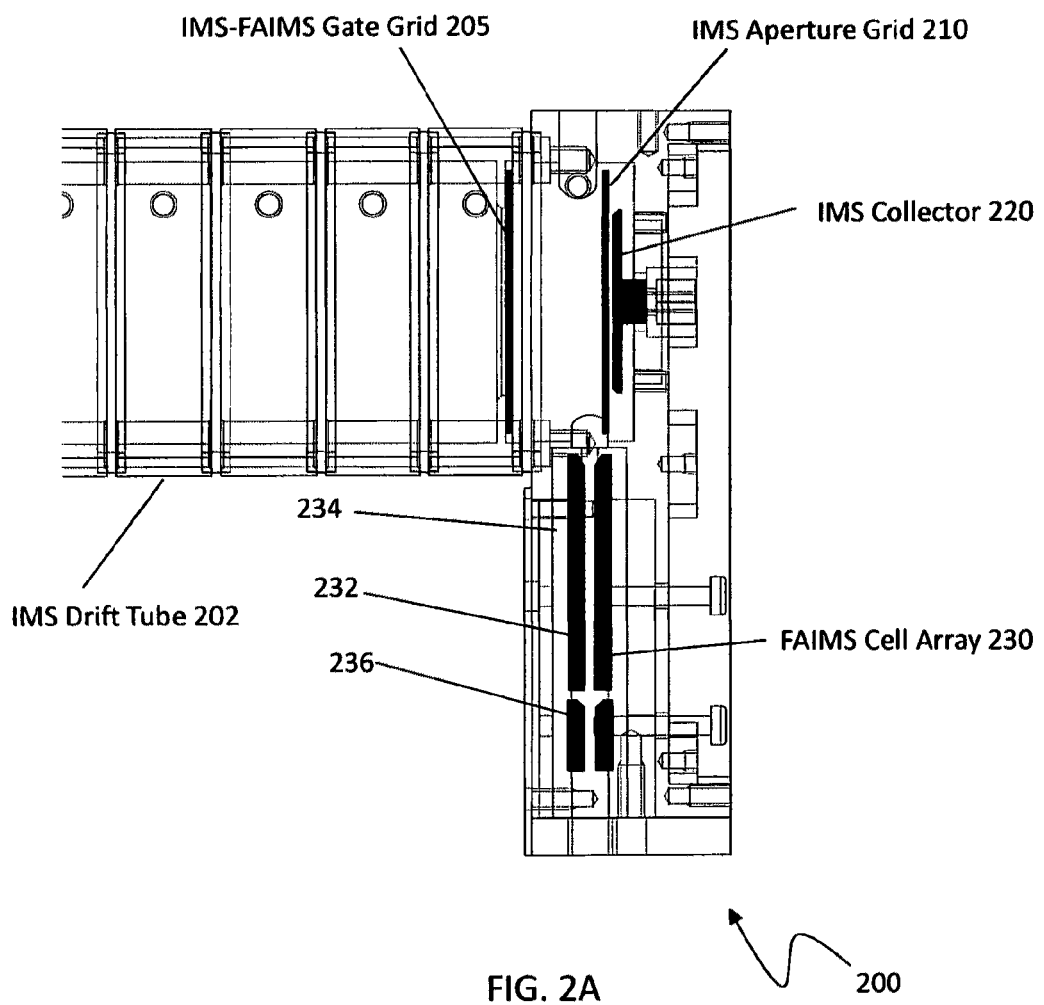
FIG. 2A is a schematic illustration showing a biased gate grid positioned at the end of an IMS drift tube according to an embodiment of the system described herein.

FIG. 2A is a schematic illustration 200 showing a biased gate grid 205 positioned at the end of an IMS drift tube 202 according to an embodiment of the system described herein.

A pulsed voltage is applied to the gate grid 205 to switch from IMS to FAIMS modes and vice versa. A FAIMS device 230 may be inserted off-axis, e.g. at 90 degrees, between the gate grid 205 and an IMS aperture grid 210 and IMS collector 220. When the voltage on the gate grid 205 is switched to zero, a field free region is established and the suspended ions are pneumatically entrained at a 90 degree angle into the cells of the FAIMS device 230 using a gas flow (see FIG. 2B). The ion evacuation time determines the number of grid pulses per sampling cycle. The IMS aperture grid 210 may establish a field in the trap volume and guide ions towards the IMS collector 220.

In an embodiment, the FAIMS device 230 may include five parallel stainless steel plates 232 (e.g., 5 mm wide, 15 mm long, and 1 mm thick) making four FAIMS cells intended to operate in parallel. The plates 232 may be encased and recessed in one or more supports 234 (e.g., a Polyetheretherketone (PEEK) support measuring 8 mm wide, 18 mm long, 3 mm thick) that provides mechanical stability and electrical insulation. In parallel with the FAIMS plates is another set of five shorter (e.g., 2 mm long) detector plates 236 all connected together to generate a single signal. The plates may be fastened to the supports by high temperature epoxy. Electrical connections to the individual plates are made via wires spot welded through holes in the support. The 0.5 mm spacing between the electrodes may be maintained by an insulated polymer spacer. The top and bottom plates are then secured to each other through the support and insulating polymer with screws to ensure mechanical stability and alignment.

The FAIMS device 230 is principally described herein in connection with a planar geometry design, which may offer several advantages including ease of manufacturing and superior resolution. However, in other embodiments of the system described herein, other non-planar geometry designs of FAIMS devices may also be used, including cylindrical, spherical, and/or other appropriate geometries (see, e.g., R. Guevremont, *"High-Field Asymmetric Waveform Ion Mobility Spectrometry* (FAIMS)," Canadian Journal of Analytical Sciences and Spectroscopy, Vol. 49, No. 3, 2004, pp. 105-113, which is incorporated herein by reference, for a discussion of cylindrical geometry FAIMS among other FAIMS concepts).

Figure 2B:
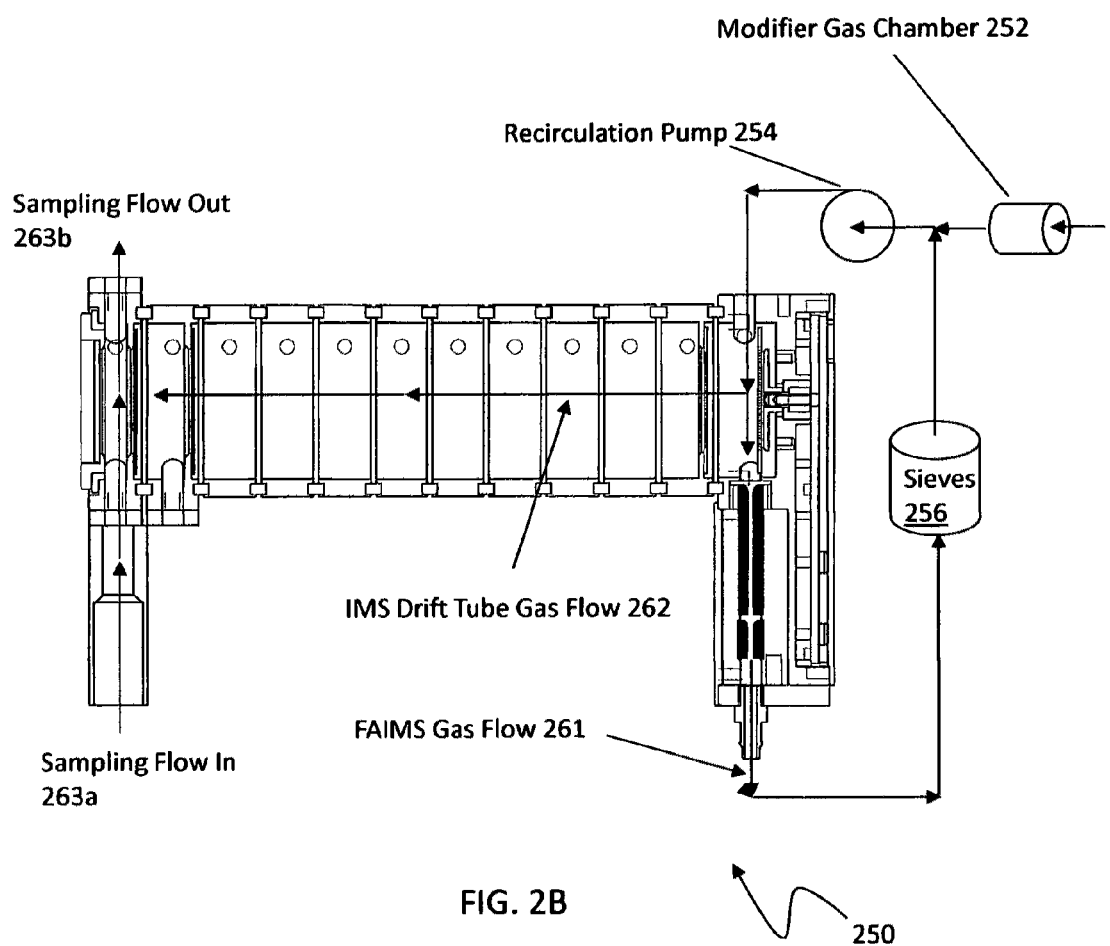
FIG. 2B is a schematic illustration showing directions of FAIMS and IMS drift tube gas flows according to an embodiment of the system described herein.

FIG. 2B is a schematic illustration 250 showing directions of FAIMS and IMS drift tube gas flows that may be used in connection with operation of the system described herein. The gas flows may include air, other gases and/or a composition of air and other gases or substances that may be generated using a modifier gas chamber 252. The illustration 250 shows the directions of the FAIMS gas flow 261 and the IMS drift tube gas flow 262. Also shown is the sampling gas flow into and out of the system (sampling gas flow in 263a and sampling gas flow out 263b). The FAIMS gas flow 261, which can be set, for example between two and ten liters per minute, may be circulated through one or more molecular sieves 254 using a pump 256. As further discussed elsewhere herein, ions are propelled through the IMS drift tube 202 in a controlled manner and are injected into the FAIMS gas flow 261 and driven thereby into the analytical gap of the FAIMS device 230. It is noted that, in the embodiment shown, the IMS drift tube gas flow 262 may be in the opposite direction of the flow of ions propelled through the IMS drift tube and injected into the FAIMS gas flow 262.

Figure 3A:
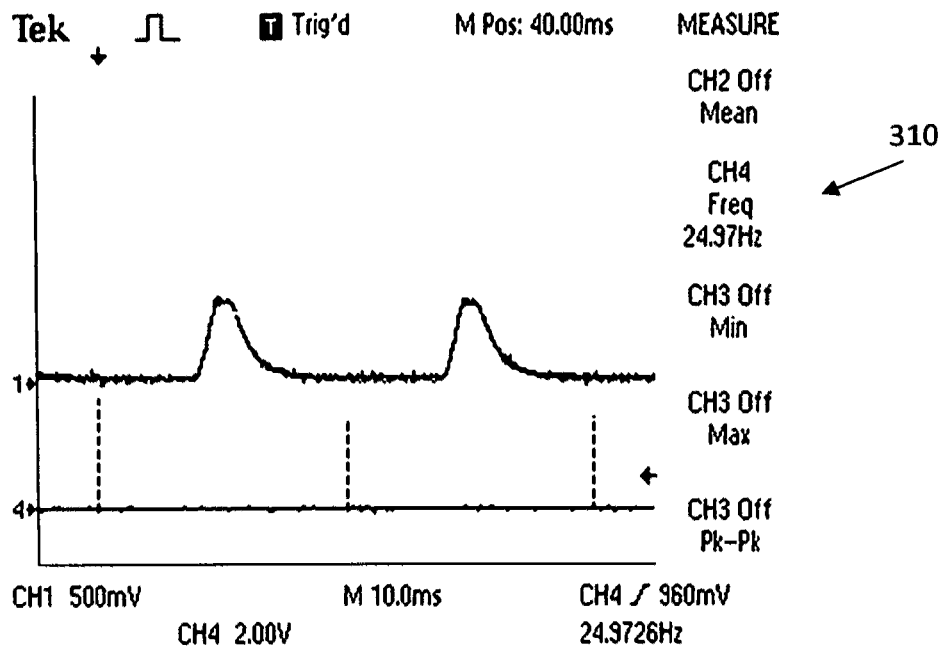
FIGS. 3A and 3B are schematic illustrations showing characteristics of two operational modes, such as an IMS mode and a FAIMS mode, of the system.
Figure 3B:
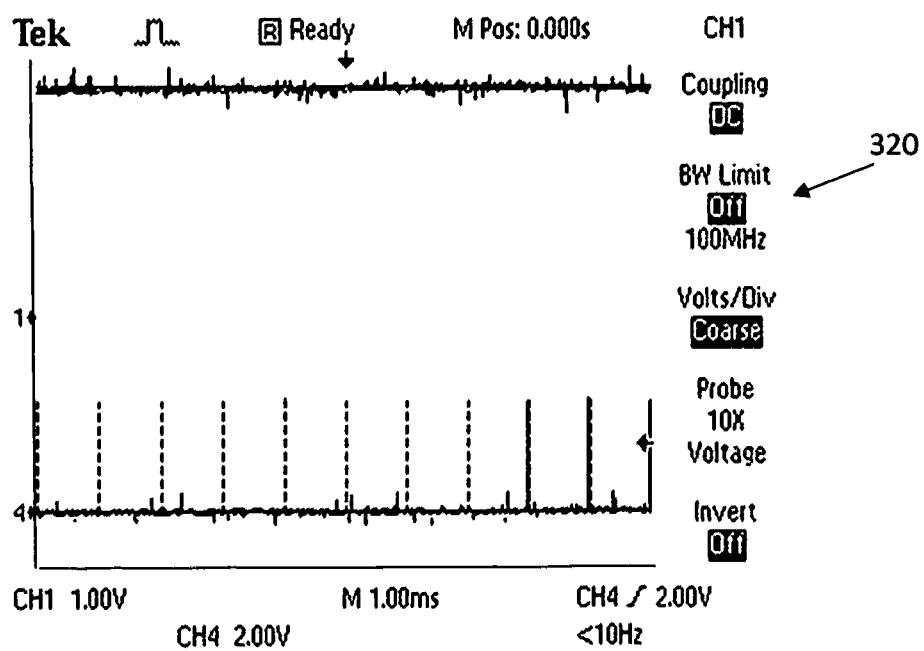

FIGS. 3A and 3B are schematic illustrations showing characteristics of two operational modes, e.g., an IMS mode and a FAIMS mode, of the system 100 that may alternate depending on the voltage bias of the gate grid and the frequency of the spark ion source according to an embodiment of the system described herein. FIG. 3A is an illustration 310 showing the characteristics for a spark ion source at 25 Hz and FIG. 3B is an illustration 320 showing the characteristics for a spark ion source at 1 kHz. The top trace in each figure shows the IMS detector response. In IMS mode, packets of ions may be injected into the IMS drift tube at a low frequency, e.g. 12 Hz, and in the FAIMS mode, the frequency can reach 1 kHz. At such a high frequency, the spark is a continuous source of ions for the FAIMS. More signal (e.g., a factor of 10) may be obtained at higher spark frequencies. Higher signals may be obtained in the FAIMS mode by increasing the field in the drift tube which becomes an ion guide.

Figure 4:
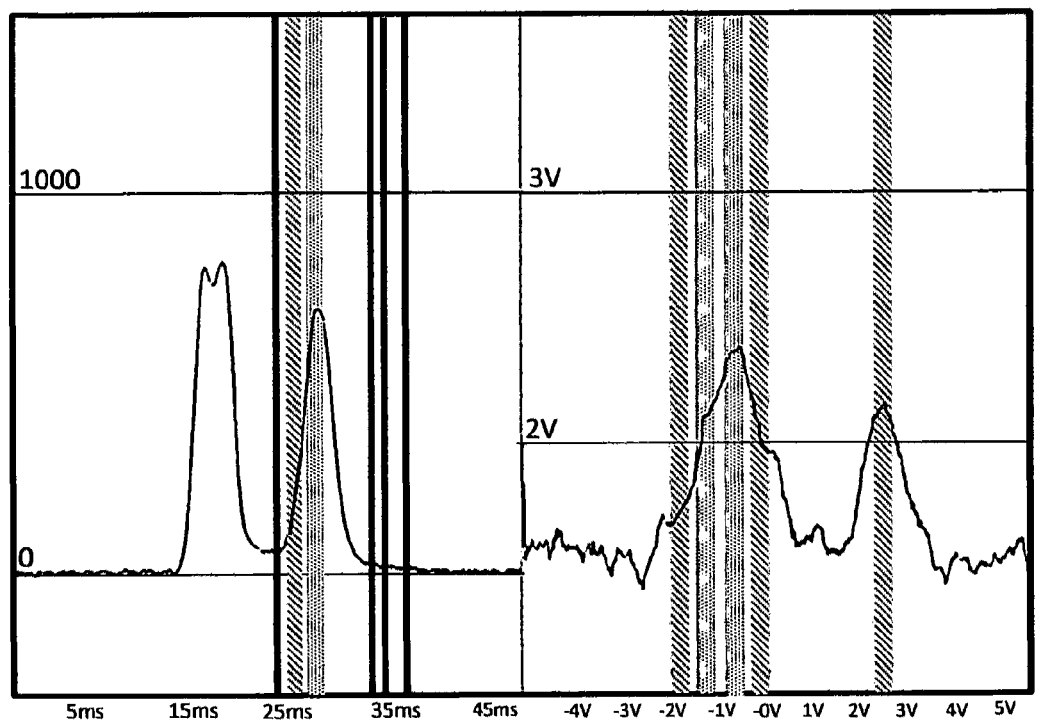
FIG. 4 is a schematic illustration showing juxtaposition of an IMS spectra and FAIMS spectra according to an embodiment of the system described herein

FIG. 4 is a schematic illustration 400 showing juxtaposition of an IMS spectra and FAIMS spectra according to an embodiment of the system described herein. The low level flexibility of this approach results in different modes of operation exploiting the trade-offs between selectivity, sensitivity, and speed. An example of an operation scenario during a sampling cycle would include generating a conventional IMS chromatogram and, upon detecting a peak, automatically switch to FAIMS mode by tuning the filter to the CV value of the detected peak. A detected FAIMS signal would serve as a confirmation as in the case of the IMS and FAIMS spectra for C4 juxtaposed in FIG. 4. Unresolved peaks in the IMS spectra corresponding to some explosives such as TNT and interferents such as hand cream but resolved in the FAIMS spectra may also be provided in accordance with the system described herein.

The IMS-FAIMS arrangement according to the system described herein provides advantageous flexibility and several other modes may also be used in connection with the system described herein. For example the gate grid 210 (FIG. 2) may serve as a gate for ions of interest. In other words, by applying a short pulse to the grid 210 at a certain time in the IMS spectrum only ions with a specific drift time will be transmitted into the field free region for FAIMS analysis. The system described herein thereby enables enhanced control for detecting ions of interest by controlling the ions that are transmitted to the FAIMS device 230 through the control of pulses corresponding to the specific drift times of the ions of interest.

The shape of a drive waveform for a FAIMS device is one of the features affecting FAIMS' resolution, transmission, and separation. Due to practical circuitry advantages, most FAIMS work to date has employed a waveform formed by summing a sinusoidal wave and its first harmonic, at twice the frequency (Equation 2), resulting in first order Fourier approximation of an asymmetric square wave.

Figure 5A:
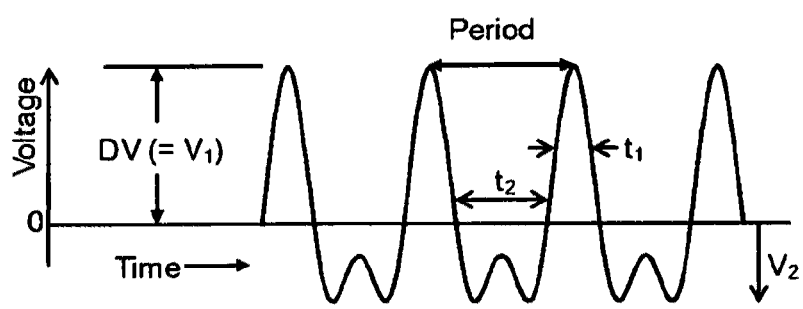
FIG. 5A is a schematic illustration showing an asymmetric sum-of-sine waveform for driving a FAIMS device.

FIG. 5A is a schematic illustration showing an asymmetric sum-of-sine waveform for, being the first order Fourier approximation of an asymmetric square wave, for driving a FAIMS device. The shape of the waveform is a parameter that contributes to the value of the experimentally measured (compound-dependent) CV for transmission of an ion. A symmetrical waveform (sine or square) should result in CV=0 V for transmission of all types of ions. Asymmetry of the waveform is required for ion separation, and is expressed by differences in the CV values.

According to the system described herein, it has been determined that a rectangular drive waveform may be advantageous for FAIMS analyses. Analytical considerations show that rectangular waveforms may improve ion separation efficiency, resolution and/or sensitivity as compared to sinusoidal waveforms. Unfortunately, the excessive power load imposed by high frequency, high voltage pulses with steep rise times has hindered the development of electronics that deliver rectangular pulses for driving separations based on differential ion mobility.

Intuitively, the use of an asymmetric square (and/or other rectangular) waveform for FAIMS would seem to maximize the differences during the high and low field portions of the electric field. These high to low periods of the waveform permit an ion to experience a maximum of unequal voltages maximizing the CV. However, in previous studies, there have been concerns that the time it takes an ion to respond to the idealized asymmetric square waveform and reach "steady state," or terminal, drift velocity might be sufficiently long to introduce error due to the transient electric field. It has been shown that, to the first order, this can be neglected if the time for reaching terminal velocity is small relative to the total drift time. Since the estimated time necessary to reach this velocity in a transient electric field is in the picosecond range and the drift time is in the millisecond range, this factor can therefore be ignored.

Figure 5B:
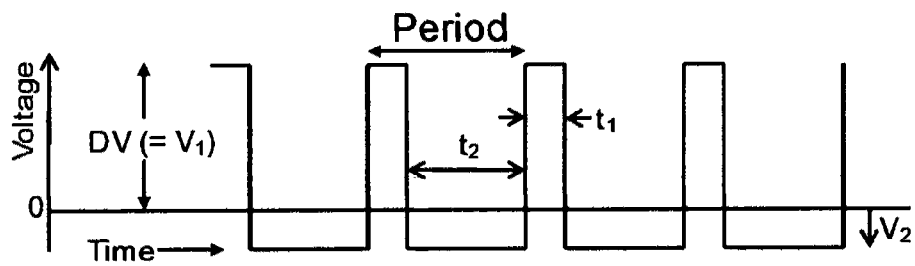
FIG. 5B shows a rectangular waveform that may be used in connection with driving a FAIMS device according to the system described herein.

FIG. 5B shows a rectangular waveform that may be used in connection with driving a FAIMS device according to the system described herein. In an embodiment, the system described herein provides for generating a square waveform to drive the FAIMS device. The method may include using direct transistor switching at high speed and at reasonable power losses. The choice of high voltage (>1000 V) fast transistors (FETs) with low output capacitance may be limited. On one hand, the 1500 V transistors are very slow and on the other, the 1200 V FETs have large output capacitances making the switching at high speed power consuming. 800 V transistors or FETs (which are fast and have low output capacitances) may also be used in series to carry very high voltages in connection with the system described herein. Other techniques may also be used in connection with generating waveforms for use with the system described herein and reference is made to, for example, E. V. Krylov, et al., "Selection and generation of waveforms for differential mobility spectrometry," Review of Scientific Instruments, 81, 024101 (2010), 11 pp., which is incorporated herein by reference.

Figure 6:
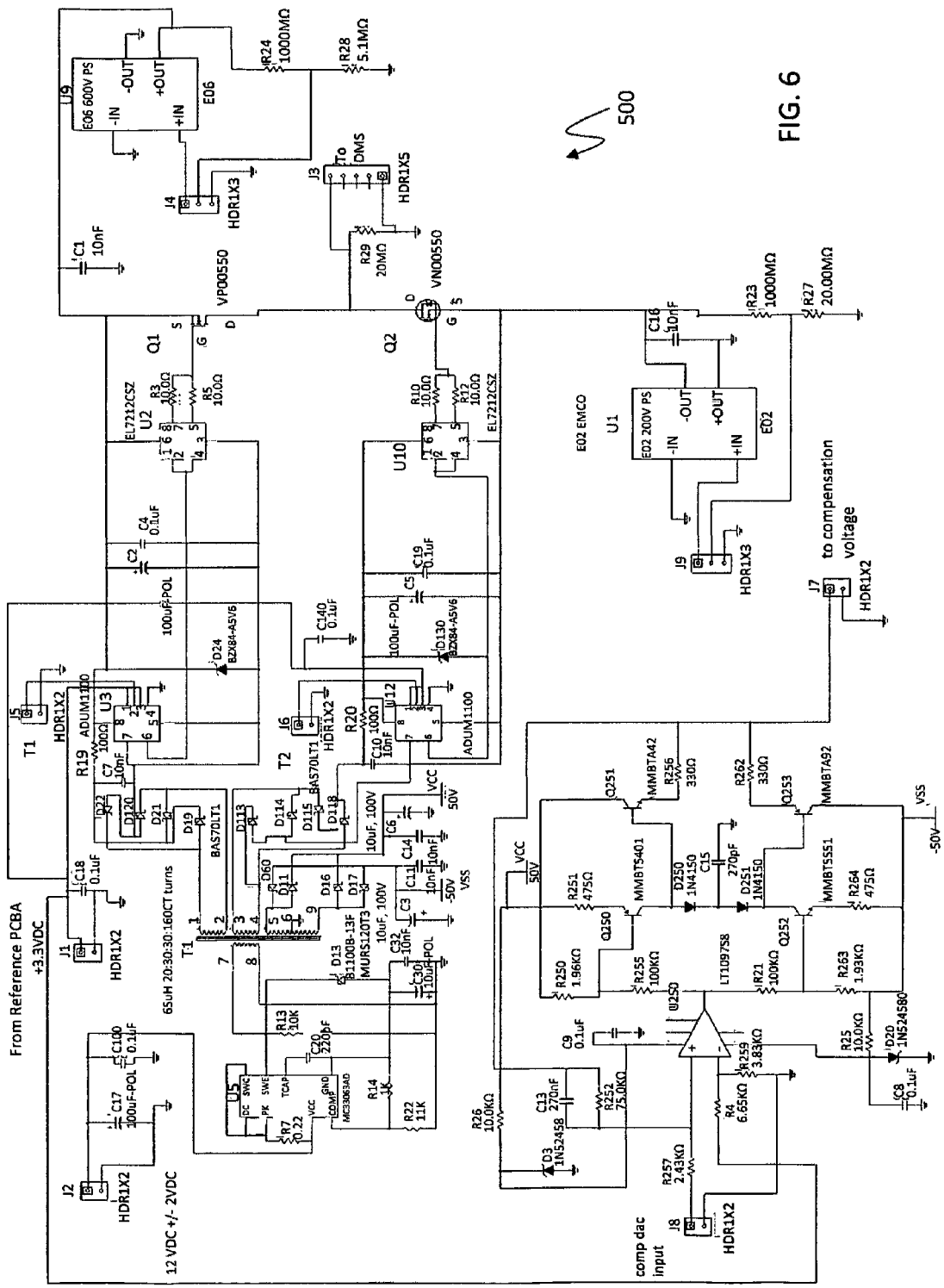
FIGS. 6 and 7 show schematic circuit diagrams for circuits that may be used according to various embodiments of the system described herein.
Figure 7:
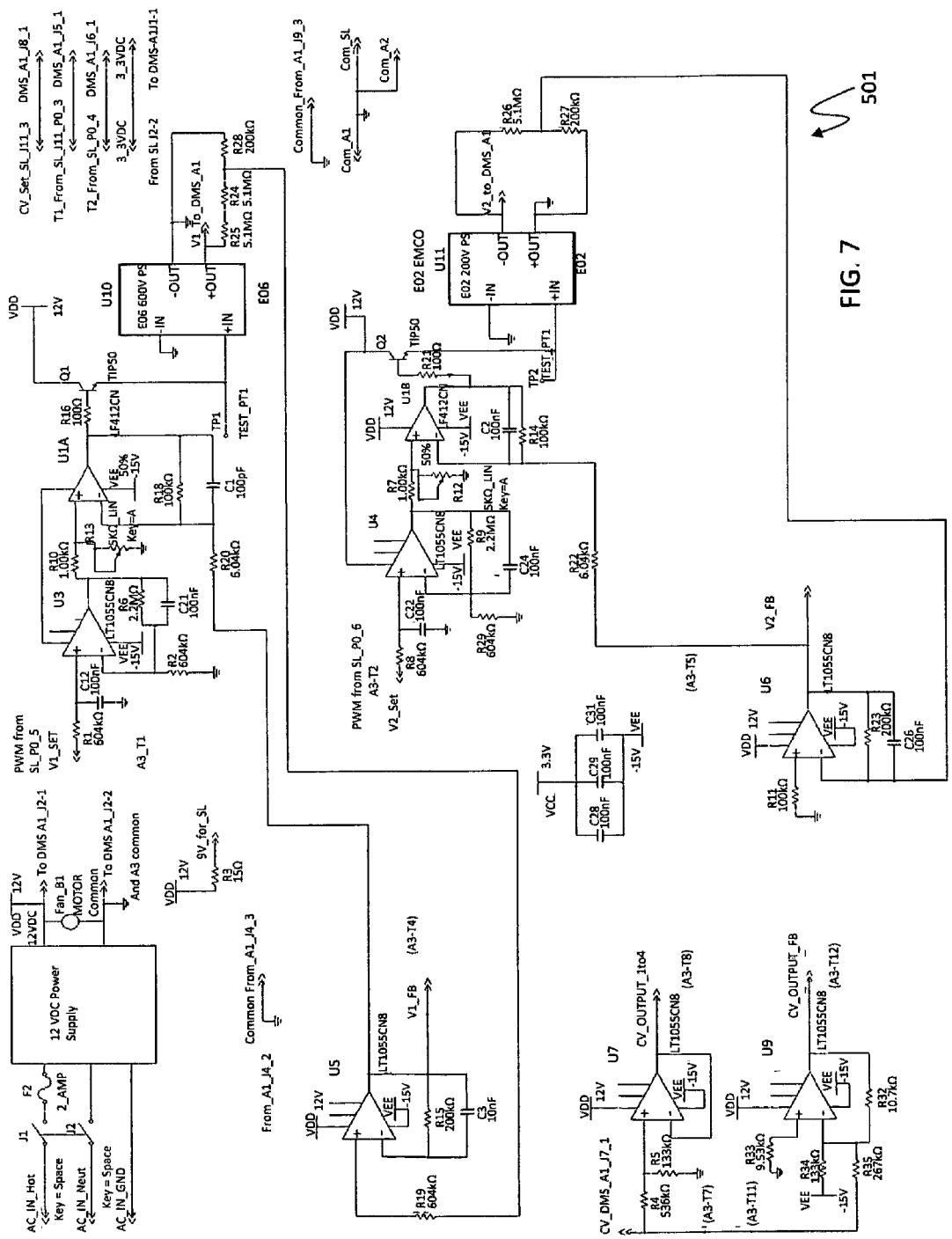

FIG. 6 shows a schematic circuit diagram 500 and FIG. 7 shows an auxiliary circuit diagram 501 for circuits that may be used according to various embodiments of the system described herein. The following modes of operation may be provided in connection with the above-noted circuits according to the system described herein:

a. V1=+1000 V; V2=−500 V at a 2:1 duty cycle.
b. V1=+1000 V; V2=−250 V at a 4:1 duty cycle.
c. V1=+800 V; V2=−200 V at a 4:1 duty cycle.

Two switching waveforms may be used, one to drive the positive voltage and one for the negative voltage. These waveforms provided for adjustments to account for the circuit peculiarities and to provide the necessary dead times to assure low power switching. Three out of the four variables (V1, V2, T1, and T2) may be settable from a computer and the fourth may be deduced from the balance Equation 3.

The FAIMS driver may include a FET half-bridge (Q1, Q2), with a bus supplied by two EMCO power supplies: +400 VDC (U9) and −100 VDC (U1) connected in series and referenced to common ground (see circuit diagrams at the end of the document). Switching output is referenced to common ground via R29 (20 MOhm). The high-side FET Q1 is P-channel and bottom FET Q2 is N-channel. It has been found that a P and N combination performs better than 2 N-channel FETs. The gate drives are provided by EL7212 drivers (U2, U10). Isolated 5.6 VDC sources are generated by the U5-T1 power supply and R19, D24/R20, D130 zeners. U3, U12 (ADUM1100) provide HV isolation and transfer from 3.3V to 5.6V signals. The logic drive signals and 3.3V bus may be provided by the outside reference board. The main source of power losses in illustrated circuits with low current, low inductance is charging and discharging of Coss of the FETs themselves. However the low Coss, high Voltage FETs may be designed for low power applications, packaged in TO-92 and cannot handle losses higher than 1 W per FET. It is also that various aspects of the circuits shown in FIGS. 6 and 7 may be simulated using computer software.

Figure 8:
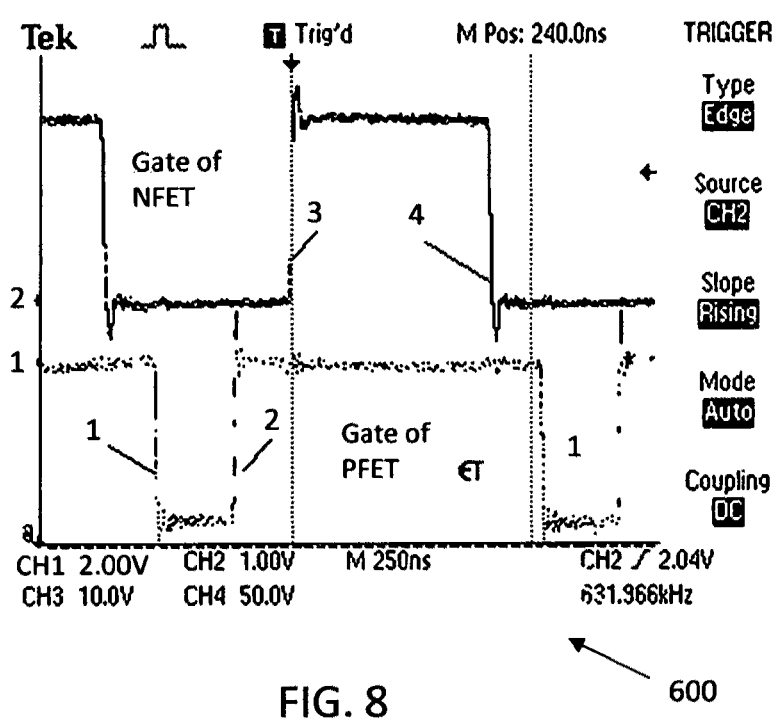
FIG. 8 is a schematic illustration showing output P and N channel gate drive waveforms according to an embodiment of the system described herein.

FIG. 8 is a schematic illustration 600 showing output P and N channel gate drive waveforms according to an embodiment of the system described herein. The 2-3 and 4-1 intervals shown on the figure are circuit dead times. The negative front 1 turns on PFET Q1 (Q2 is OFF) and brings output to +400 VDC. From 1 to 2, Q1 discharges its own Coss (approx. 10 pF) and charges Q2 Coss (approx. 8 pF) by 500V. Q1 charging Q2 Coss losses may be accounted for as conduction losses. The positive front 3 turns on NFET Q2 (Q1 is OFF) and brings output to −100 VDC. From 3 to 4 Q2 discharges its own Coss and charges Q1.

While discharge losses are may be calculated as P=V2*Coss/2, the charge losses inside the FET due to Coss dissipation are not defined. As a first approximation, charging Coss losses may be assumed to dissipate partially in the power source resistance and partially in the opposing FETs' Rds (on).

Figure 9:
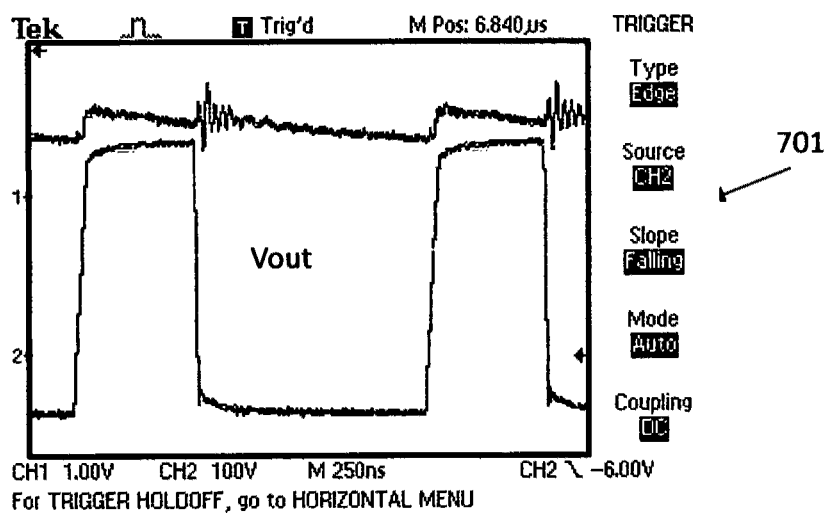
FIGS. 9-11 are schematic illustrations showing output results according to an embodiment of the system described herein.
Figure 10:
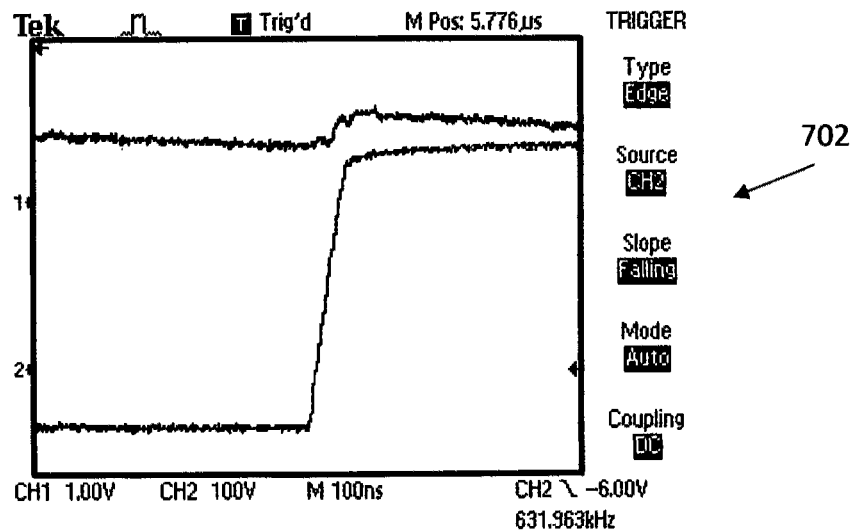
Figure 11:
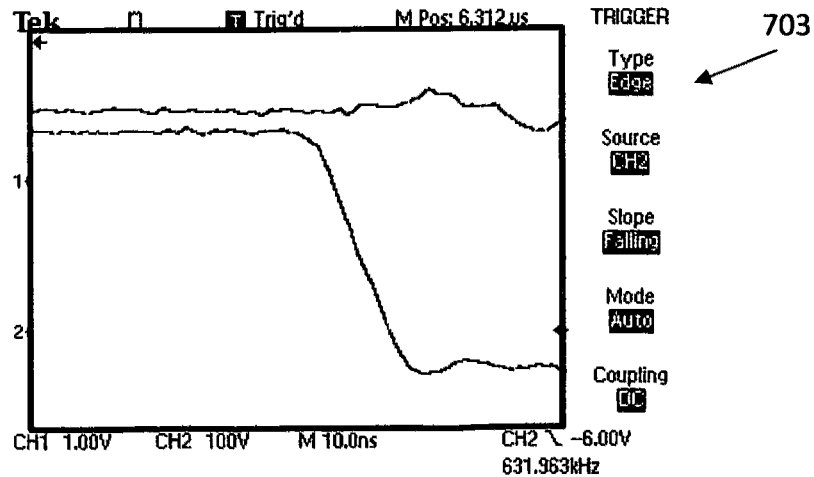

FIGS. 9-11 are schematic illustrations showing output results according to an embodiment of the system described herein. FIG. 9 is a schematic graph 701 showing a FAIMS driver output. FIG. 10 is a schematic graph 702 showing Vout—rise at higher resolution (rise time is 50 ns at dv/dt of 10V/ns). FIG. 11 is a schematic graph 703 showing Vout fall at higher resolution (fall time is 10 ns at dv/dt of −50V/ns). The horizontal slope of the output signal is due to poor instrumentation—100× probe. The gate drives of Q1, 3 selected to be 6V to maximize switching speed and reduce Coss losses. The maximum frequency of operation based on current FETs-VP0550 and VN0550 with Aavid 5725000B heat sinks should be limited to below 250 KHz to avoid destructive junction temperatures.

Two switching waveforms may be used in connection with the output, one to drive the positive voltage and one for the negative voltage. These waveforms provide for adjustments to account for the circuit peculiarities and to provide the necessary dead time to assure low power switching. Computer simulations may be used to optimize the switching scheme and hence obtain a waveform at a total power of only 0.5 watts. The computer, if desired, can continuously adjust the time portion shape of the waveform. The voltage portion of the wave shape can be adjusted but not at the high rate at which the time can be adjusted at the present time. The upper voltage and the upper time may be input as well as the lower voltage and the lower time, but is planned in operation to only vary the lower time (T2). The test set up includes the ability to set the compensation voltage to be applied to the lower electrode of the FAIMS, although an adjustable lower voltage time may also be used instead of a compensation voltage. Using this technique to keep the ions in the middle of the path so as not to strike the electrodes allows a substantial amount of circuitry to be eliminated. By adding CV to the waveform the energy is changed by (T1−T2)*CV. By changing T2 from the nominal value given by T1*V1=T2*V2 the energy is changed by the difference in T2 times V2. Therefore the equivalence can be determined if one wants to correlate both types of data taken under similar circumstances. The use of a variable T2 represents a considerable saving in circuitry and power.

Figure 12A:
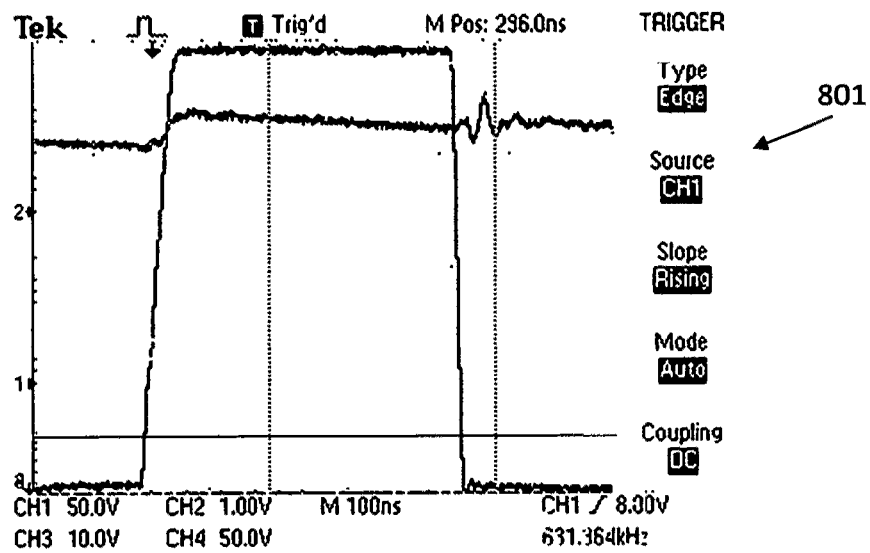
FIGS. 12A and 12B are schematic illustrations showing rectangular asymmetric waveforms usable to drive FAIMS devices along with the current required to generate such high voltages.
Figure 12B:
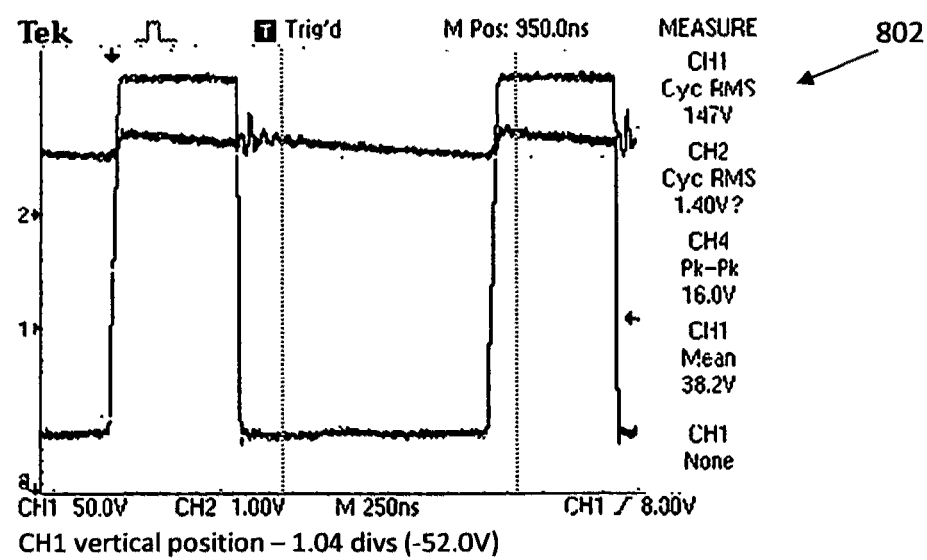

FIGS. 12A and 12B are schematic illustrations showing rectangular asymmetric waveforms usable to drive FAIMS devices along with the current required to generate such high voltages. FIG. 12A is a graph 801 showing a 500 ns up time at 400 volts. The upper curve is the current at 5 ma per div. FIG. 12B is a graph 802 showing a 30 ns rise time and faster fall time.

Figure 13:
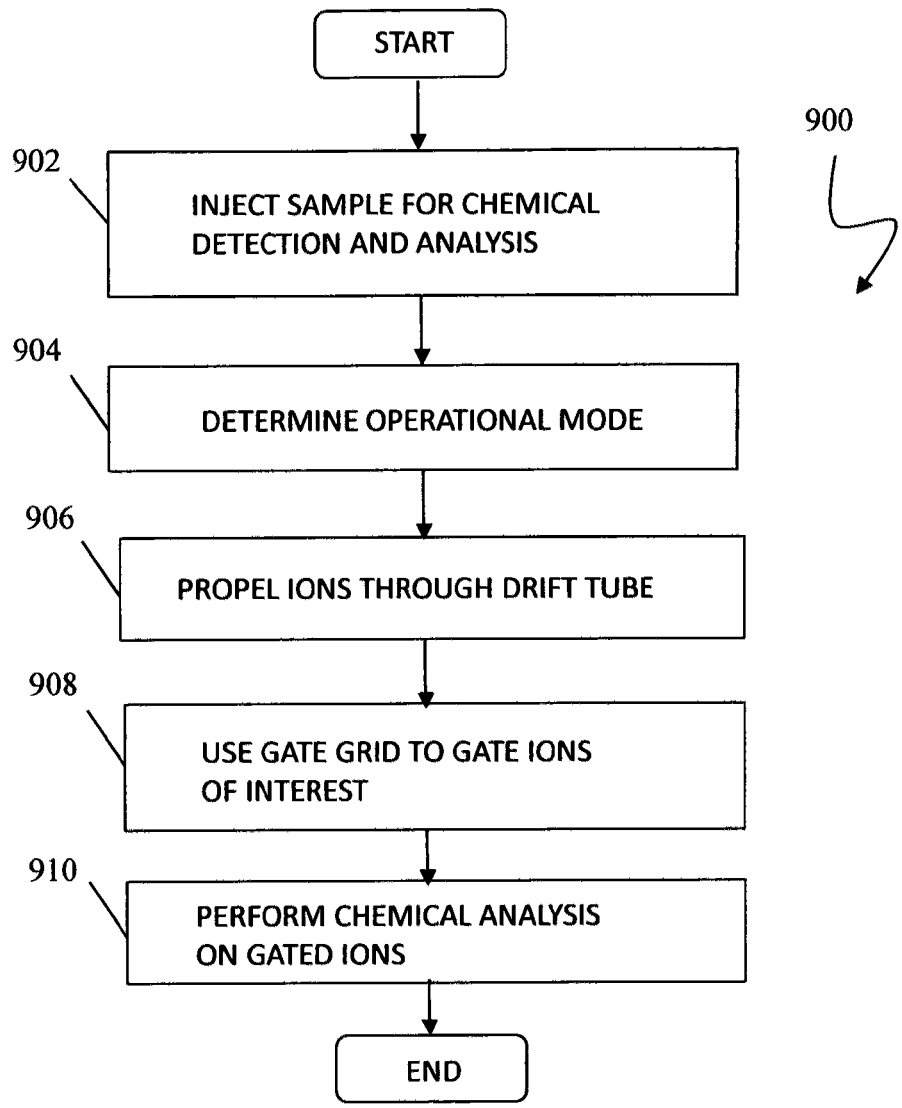
FIG. 13 is a flow diagram showing chemical analysis and detection processing steps according to an embodiment of the system described herein.

FIG. 13 is a flow diagram 900 showing chemical analysis and detection processing steps according to an embodiment of the system described herein. At a step 902, a sample gas on which chemical analysis and detection is to be performed is provided through a sample inlet to a IMS/FAIMS system according to that described herein. After the step 902, processing proceeds to a step 904 where the operational mode of the system is determined, for example, an IMS and/or FAIMS operational mode. It is also noted that operational modes may be changed during processing. After the step 904, processing proceeds to a step 906 where ion mobility spectrometry processing is performed using the IMS device, in which the sample is ionized and the ions are propelled through a drift tube, and in which the ions are separated according to drift time according to the determined operational mode. The frequency of the ion source may be determined by the operational mode. After the step 906, processing proceeds to a step 908 where a gate grid is controlled according to the determined operational mode. For example the gate grid may serve as a gate for ions of interest by applying a short pulse to the grid at a time in the IMS spectrum such that only the ions with a specific drift time, corresponding to application of the pulse to the grid, will be transmitted into the analytical gap of the FAIMS device. After the step 908, processing proceeds to a step 910 where chemical analysis is performed on the ions that have been separated and directed (gated) according to the system described herein. For example, in FAIMS mode, the FAIMS device may be used according to FAIMS techniques to analyze the gated ions of interest. After the step 910, processing is complete.

According to the system described herein, a chemical detection and analysis system includes an ion mobility spectrometer (IMS) device having a drift tube that includes a first end with a sample inlet and a second end that is downstream from the first end. Ions from ionization of a sample input via the sample inlet are introduced into the drift tube. A gate grid is coupled to the second end of the drift tube. A high field asymmetric waveform ion mobility spectrometer (FAIMS) device is coupled downstream from the gate grid, wherein the ions from the drift tube are selectively gated for analysis by the FAIMS device via control of at least one voltage pulse to the gate grid. The FAIMS device may be coupled orthogonally to a flow direction of the ions through the drift tube of the IMS device. Control of the at least one voltage pulse to the gate grid may correspond to drift time of an ion of interest. The FAIMS device may include a circuit that drives the FAIMS device using an asymmetrical waveform, such as a rectangular waveform, although other asymmetrical waveforms may also be used. The system may operate in at least two operational modes corresponding to operations of the IMS device and the FAIMS device. The FAIMS device may have a planar or non-planar geometry.

According further to the system described herein, a method for performing chemical detection and analysis includes ionizing a sample in an ion mobility spectrometer (IMS) device having a drift tube that includes a first end with a sample inlet and a second end that is downstream from the first end. Ions from ionization of the sample are introduced into the drift tube. The method further includes controlling at least one voltage pulse to a gate grid coupled to the second end of the drift tube to selectively gate ions for analysis. An analysis on the gated ions is performed using a high field asymmetric waveform ion mobility spectrometer (FAIMS) device coupled downstream from the gate grid. The FAIMS device may be coupled orthogonally to a flow direction of the ions through the drift tube of the IMS device. The control of the at least one voltage pulse to the gate grid may correspond to drift time of an ion of interest. The FAIMS device may be driven using an asymmetrical waveform, such as a rectangular waveform, although other asymmetrical waveforms may also be used. The method may further include controlling operations in connection with at least two operational modes corresponding to operations of the IMS device and the FAIMS device. Characteristics of the ionization of the sample may be determined according to a particular operational mode of the at least two operational modes. The FAIMS device may have a planar or non-planar geometry. The method may further include using at least one gas flow to enhance separation of ions in the FAIMS device, and in which the at least one gas flow includes at least one of: air, a gas other than air, or a mixture of air and other gases or substances.

According further to the system described herein, a non-transitory computer readable medium stores software for controlling chemical detection and analysis processes. The software includes executable code that controls ionizing of a sample at a frequency determined according to an operational mode of a chemical detection and analysis system. Executable code is provided that determines a drift time of an ion of interest through a drift tube of an ion mobility spectrometer (IMS) device. Executable code is provided that controls at least one voltage pulse of a gate grid coupled to the drift tube of the IMS device, in which controlling selectively gates ions for analysis by a high field asymmetric waveform ion mobility spectrometer (FAIMS) device coupled downstream from the gate grid. Control of the at least one voltage pulse to the gate grid corresponds to drift time of an ion of interest. The FAIMS device may be driven using an asymmetrical waveform, such as a rectangular waveform, although other asymmetrical waveforms may also be used. Executable code may be provided that controls operations in connection with at least two operational modes corresponding to operations of the IMS device and the FAIMS device.

As discussed elsewhere herein, it has been noted that there are synergistic benefits in combining analytical instruments. The chemical information obtained and the characteristics of the measurements are improved by more than the individual results put together. Various combinations include instruments performing the separation in either similar or different time domains and measuring the same or different properties of the species to be analyzed. Hyphenated (Instrument A/Instrument B) platforms such as Gas Chromatography (GC)-Mass Spectrometry (MS) and Ion Mobility Spectrometry (IMS)-MS are examples whereby instrument B can generate several spectra during the separation performed using instrument A. The combination of instruments A and B is mutually beneficial since the information generated by system A is enriched by system B, and system B benefits form the pre-separation performed by system A hence reducing the chemical noise. In the case of instruments operating in similar time domains the two separations can occur sequentially, whereby instrument A serves as a pre-screener and instrument B as a confirmer (see S. Boumsellek and T. J. Kuehn, U.S. patent application Ser. No. 11/941,939, filed Nov. 17, 2007, which is incorporated herein by reference). In such a scenario the mode of operation of instrument A can be optimized in order to optimally exploit the trade-offs between overall sensitivity and selectivity.

Hyphenated platforms, such as a FAIMS-MS and/or FAIMS-IMS, may be provided in which instrument A (FAIMS) may serve as a filter and/or a pre-concentrator continuously feeding instrument B (MS or IMS) with selected ions. A variation of the latter platform, in which instrument A and B are reversed (IMS-FAIMS) has been described in detail elsewhere herein, including use of a gate grid, and benefits from the drift gas of instrument A, which stops sample chemical reactions outside the ion source as well as moisture clustering effects.

In the above-noted A/B platforms, as separation stages are juxtaposed, the chemical signal-to-noise is improved since the noise decreases faster than the signal. While overall selectivity is vastly improved sensitivity is a challenge since there are inevitable sample (in either neutral or ion form) losses due to transmission inefficiencies after each subsequent stage. This is easily explained by the fact that hyphenating instruments in the conventional sense requires: (1) interfacing devices with different acceptance areas in most cases and (2) that each device has to have its own detector. Both result in increased complexity of the interface by designing restrictors, deflector, etc., causing losses of precious sample. In the case of tandem configurations, instrument B should generally have sensitivity equal or greater than that of instrument A. This means instrument B should generally either, have an inherent sensitivity that is greater than that of instrument A and/or operate in total ion mode in order to inject more sample neutrals or ions.

In view of the above, various embodiments of the system described herein may be further provided in which an instrument according to an embodiment of the system described herein combines conventional and differential mobility separation techniques in further advantageous ways. In particular, contrary to the conventional method of interfacing instruments A and B by juxtaposing them and then designing the interface, according to a further embodiment of the system described herein, instrument B may be embedded within instrument A in such a fashion that the individual functionalities of the instruments A and B are maintained in order to produce 2-D data sets. In a particular embodiment, instrument A may be an ion mobility spectrometer (IMS) and instrument B, embedded within instrument A, may be a high field asymmetric ion mobility spectrometer (FAIMS). Contrary to conventional FAIMS, where the ions are dispersed radially while moving axially through the cell, the two motions (e.g., IMS drift motion and FAIMS oscillation) may be along the same axis (the IMS drift tube axis) in the instrument A-with-embedded-B instrument according to the system described herein.

In addition to known IMS and FAIMS spectra, IMS spectra featuring drift times reflecting both weak and high-field mobilities may be recorded. In the FAIMS cell, ions may be subject to both the weak IMS field as well as the high-field of the asymmetric waveform of the FAIMS. By performing oscillations within the FAIMS cell the ions are either accelerated or decelerated depending on whether the high field mobility (KH) is higher (type A) or lower (type C). Upon applying the high frequency field, shifts along the drift time axis of the IMS spectrum, of various amounts depending on the compounds, are observed including with the reactive ions. This represents an additional dimension for separation that combines low and high properties of the mobility of the species into the same spectrum.

It is noted that the embedded FAIMS according to the system described herein does not require gas flow to pneumatically transport the ions. Accordingly, the embedded FAIMS instrument may be an all electrostatic instrument as ions are propelled under the influence of IMS and FAIMS fields. Further, the embedded FAIMS may benefit from the IMS drift gas, flowing in the opposite direction of ion travel, to eliminate ion clustering and the sensitivity to humidity. Separate flow paths for the source gas and the clean filtered gas are no longer required, thus reducing the structure required to maintain separate flow paths taught by the prior art. The two instruments may have the same acceptance area as well as the same collector for ion detection.

According to an embodiment of the system described herein, a tandem instrument using a variable frequency spark ionization source and two separation techniques, low (IMS) and high (FAIMS) field mobility is provided. The analytical stage features a field driven FAIMS cell embedded on-axis (co-axial) within the IMS drift tube. In an embodiment, the IMS drift tube may be a standard stack of rings equally spaced and appropriately biased to generate the axial drift field while the FAIMS cell is composed of two planar grid plates of the same diameter as the IMS ring electrodes. It is noted, however, that other configurations of the IMS drift tube and the grid plates of the FAIMS cell may be used in connection with the system described herein. For example, non-planar FAIMS geometries may be used as further discussed elsewhere herein.

Figure 14:
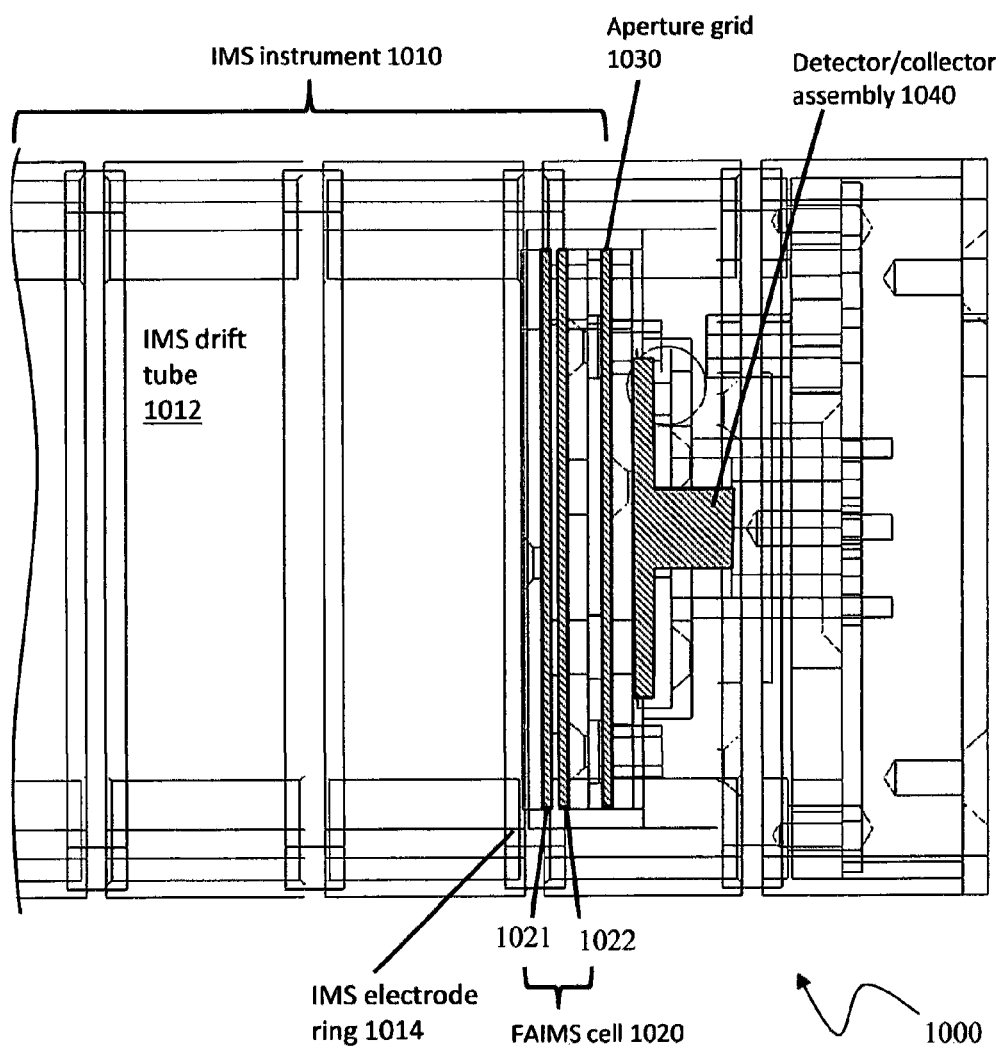
FIG. 14 is a schematic illustration of a chemical analysis and detection system showing the end of the IMS drift tube where the FAIMS cell is embedded by insertion in front of the aperture grid/collector assembly according to an embodiment of the system described herein.

FIG. 14 is a schematic illustrations showing an IMS embedded FAIMS device 1000 in which, at the end of the IMS drift tube 1012 of the IMS instrument 1010, the FAIMS instrument or cell 1020 is embedded via insertion in front of the aperture grid 1030 and detector/collector assembly 1040 according to an embodiment of the system described herein. In the illustrated embodiment, the FAIMS cell 1020 is mounted adjacent to the last electrode ring 1014 of the IMS drift tube 1012, upstream of the aperture grid/collector assembly 1030. In other embodiments, the FAIMS cell 1020 may be mounted anywhere along the entire length of the drift tube 1012. The grids 1021, 1022 of the FAIMS cell 1020, spaced by a gap (e.g., 0.5 or 0.355 mm in various embodiments) that may be referred to as the analytical gap, may have approximately the same diameter as the IMS rings of the IMS drift tube 1012 and may be biased according to their location in the voltage divider ladder to create the same IMS field. The dispersion and compensation voltages could be either both or individually applied to either one of the grids 1021, 1022.

Between the parallel grid plates of a conventional FAIMS cell, ions are subject to two orthogonal forces: (1) a dispersive force due the high frequency asymmetric field moving the ions towards either plate; and (2) a longitudinal force moving the ions from the entrance to the exit of the cell. The longitudinal force can be either pneumatic or electrostatic. Most conventional FAIMS devices feature gas flows established by pumps to pneumatically carry the ions through the cell. Such devices are called flow-driven FAIMS and require a number of additional considerations. For example, a mechanism may be required to separate the carrier gas from the ions to avoid additional chemical reactions outside the ionization source. Further, the ions acquire the local gas flow velocity during their transit through the cell. Such velocity has a parabolic profile across the gap meaning ions moving near the gap median are faster than ions moving near the plates. This leads to a distribution of residence times of the same species causing a reduction of the effective gap and therefore a loss of sensitivity. Additionally, pumps may be required to draw a sample medium into the FAIMS cell and to provide a carrier gas can be rather large and consume large amounts of power. The carrier gas should flow in the same direction as the ions, requiring a structure which separates the analytical gap from the ionization source.

In contrast, in field-driven FAIMS devices, ions are electrostatically propelled through the cell using segmented electrodes, for example. Such devices can more quickly and accurately control the flow of selected ions to produce a sample spectrum. According to the system described herein, upon entering the FAIMS cell 1020, the ions are subject to the forces of the asymmetric field making them oscillate along the axis of the drift tube 1012. Depending on the value of the mobility at high fields compared to that at low fields (some ions have higher mobility, some have lower mobility), the ions will either be accelerated or decelerated through the FAIMS cell 1020, thus causing a shift in their respective drift times, which is advantageously used to separate and detect desired ions of interest. In connection with the system described herein, FAIMS cells having parallel plate electrodes (planar geometries) are principally discussed. However, it is noted that the system described herein that may also be used with FAIMS cells having non-planar geometries, as further discussed elsewhere herein. For example, in an embodiment, a FAIMS cell having a non-planar crescent-shaped parallel electrodes may be used in connection with the system described herein, among other appropriate non-planar geometries discussed elsewhere herein.

Figure 15A:
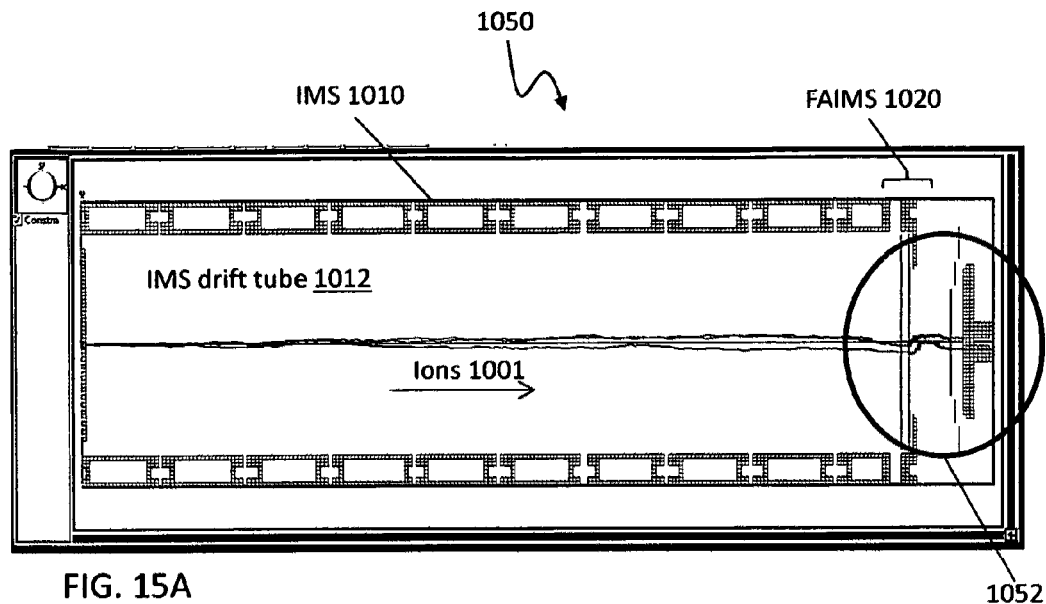
FIGS. 15A and 15B show views of an example of ion trajectories inside the IMS and through the FAIMS cell towards the collector plate to be recorded according to an embodiment of the system described herein.
Figure 15B:
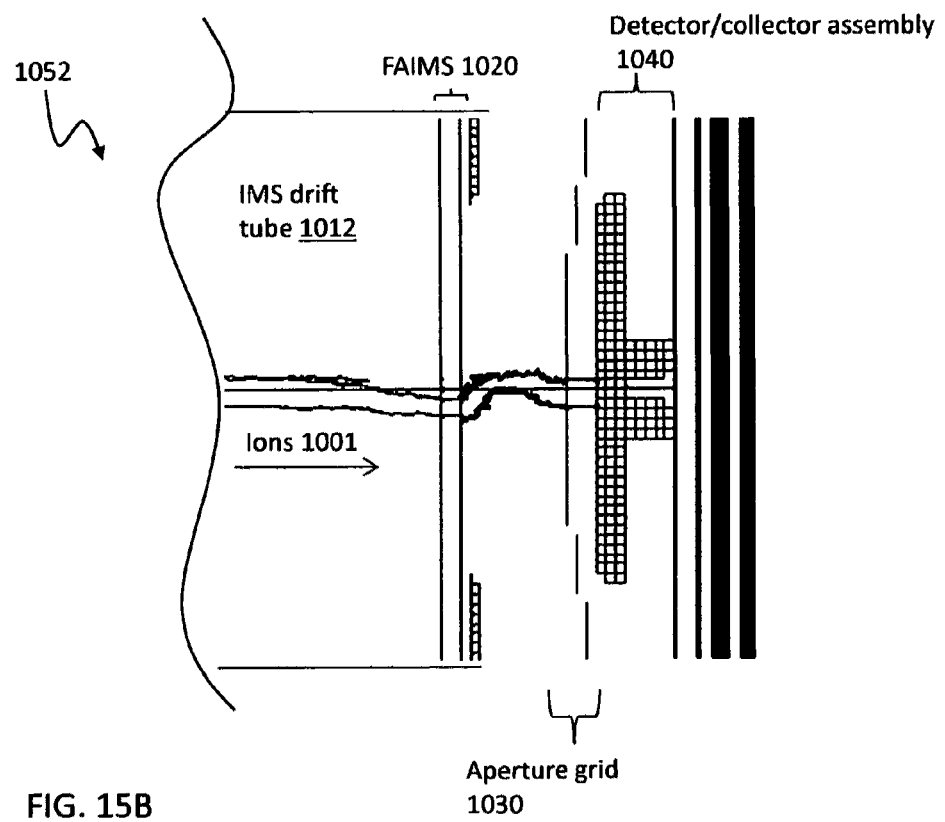

FIG. 15A is an illustration 1050 shows an example of trajectories of ions 1001 through the IMS drift tube 1012 of the IMS 1010 and through the embedded FAIMS cell 1020 towards the aperture grid 1030 to be recorded using the detector/collector assembly 1040 according to an embodiment of the system described herein. In an embodiment, the embedded FAIMS cell 1020 is field-driven. FIG. 15B is an enlarged view of the demarcated area 1052 shown in FIG. 15A. In the disclosed embodiment, a continuous stream or packets of ions 1001 move along the drift tube 1012 of the IMS 1010 and through the embedded FAIMS cell 1020 to be detected by the detector 1040. In an embodiment, the detector 1040 may advantageously be a single detector.

Ion trajectories may be calculated using known techniques. For example, ion trajectories may be calculated using the Simion ray tracing package. A user program called Statistical Diffusion Simulation (SDS) is invoked by Simion to model the ion motion at atmospheric pressure. Reference is made to A. D. Appelhans and D. A. Dahl, "SIMION ion optics simulation at atmospheric pressure," *Int. J. Mass. Spectrom,* 244 (2005), pp. 1-14, which is incorporated herein by reference. The SDS code takes into account effects of high pressure collisions by modeling both diffusional and mobility terms of ions in a neutral gas. Ion dynamics are simulated by combined viscous ion mobility and random ion jumping (diffusion) approach. Space charge effects are not included in the SDS package and may be treated separately using the Coulomb Repulsion feature built into Simion.

Figure 16A:
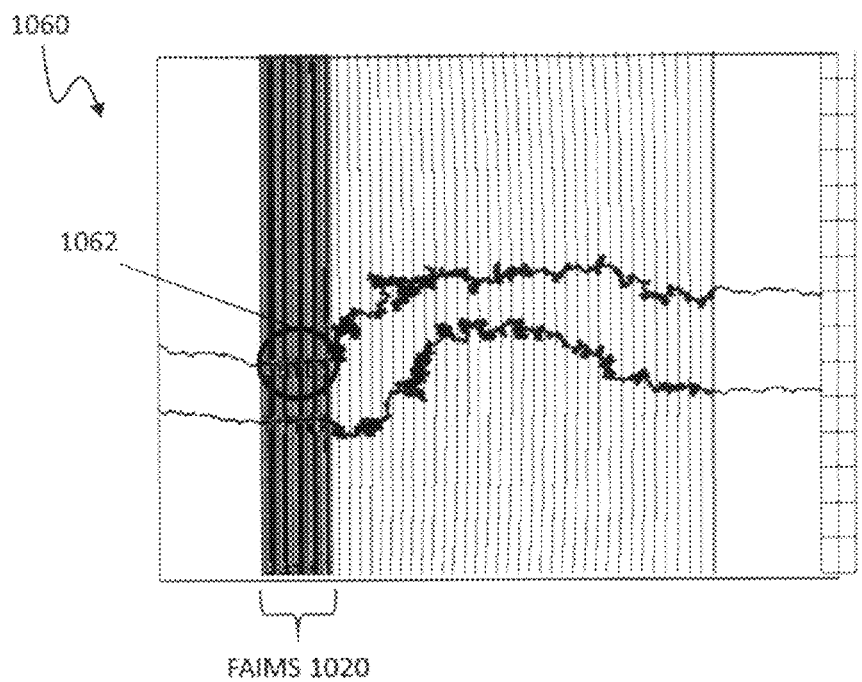
FIGS. 16A and 16B show views of ion trajectories inside the FAIMS cell, including showing oscillations of the ions, and showing diffusion effects at atmospheric pressure according to an embodiment of the system described herein.
Figure 16B:
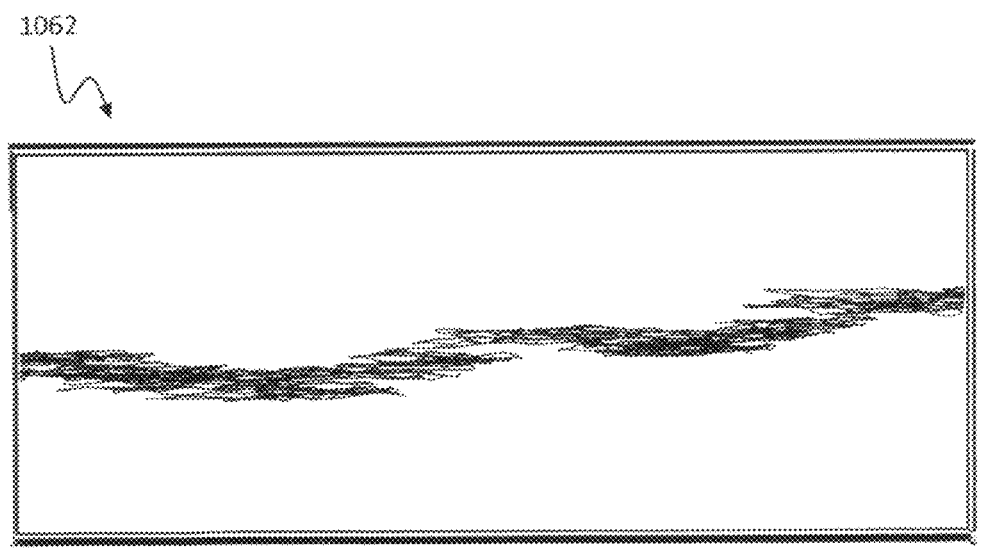

FIG. 16A is a schematic illustration 1060 of ion trajectories through the FAIMS cell to 1020 and thereafter to the aperture grid/collector assembly 1030/1040. FIG. 16B illustrates an enlarged view of the inside of the FAIMS cell 1020, indicated by an area 1062 shown in FIG. 16A, showing ion oscillations due to the high frequency dispersive field and a resulting net change in velocity of the ions. Upon entering the FAIMS cell 1020, the ions experience both a mobility due to the low IMS field and oscillations due to the high frequency of the asymmetric waveform of the dispersion voltage. It is noted that the figures also show a slight radial displacement of the ions that may result from diffusion effects at atmospheric pressure rather than being due to the electrical forces of the asymmetric field, at least for ions closer to the main axis where fringing fields are negligible.

The asymmetric waveform features a high voltage component causing the ion mobility to change with the field. As a consequence, a net change in the velocity of the ions, characteristic of the analyzed ions, results from the oscillations between high and low fields. Such a net change in the velocity may be either positive or negative for different ions. Depending on the nature of the mobility of the ions at high fields compared to that at low fields, the ions will either be accelerated or decelerated through the cell (and even including being stopped), thus causing the shift in their respective drift times that enables the desired ion separations for purposes of measurement. Accordingly, the FAIMS cell 1020, provided a stream of ions obtained by operating the ionization source at a high frequency, serves as a gate filtering ions or classes of ions depending on the value of a DC voltage (called compensation voltage) applied to either one of the FAIMS grids. Scanning such a DC voltage generates a spectrum. As discussed elsewhere herein, the ionization source used in connection with the system described herein may be a pulsed ionization source, such as a spark ionization source, and/or may be a continuous ionization source, in which case one or more ion gates may be added at operated at a variable frequency.

A second mode of operation according to the system described herein includes temporarily disabling the IMS field while setting the compensation voltage at a value that causes certain species to be trapped inside the FAIMS cell 1020. In this mode, the compensation voltage would be called a trapping voltage. During the trapping time, species of interest are being pre-concentrated as other compounds either strike the grid wires or leave the FAIMS cell 1020. Following this time the IMS field is tuned back ON and an enriched signal of the species of interest is recorded. This mode can be utilized for confirmation purposes when the IMS is inconclusive. In fact, an interference observed in the IMS spectrum can be resolved upon triggering this mode using trapping voltages characteristic of various species stored in a database.

A third mode of operation includes using ion packets injected, via ions gates from a continuous ion source such as beta emitters, corona, or electrospray, or directly from the spark ion source operating at low frequency, into the drift tube recording traditional IMS chromatograms. Such chromatograms feature flight times which combine: (1) conventional ion drift time at low field and (2) time spent by ions inside the FAIMS cell as they perform several oscillation cycles prior to exiting. Depending on their mobility at high fields some ions will move faster through the cell and other will move slower resulting in time shifts in the traditional IMS spectrum. In sum, two separation methods, conventional and differential mobility, contribute to the drift times in the new IMS spectra hence enhancing instrument selectivity by resolving interferences.

Figure 17:
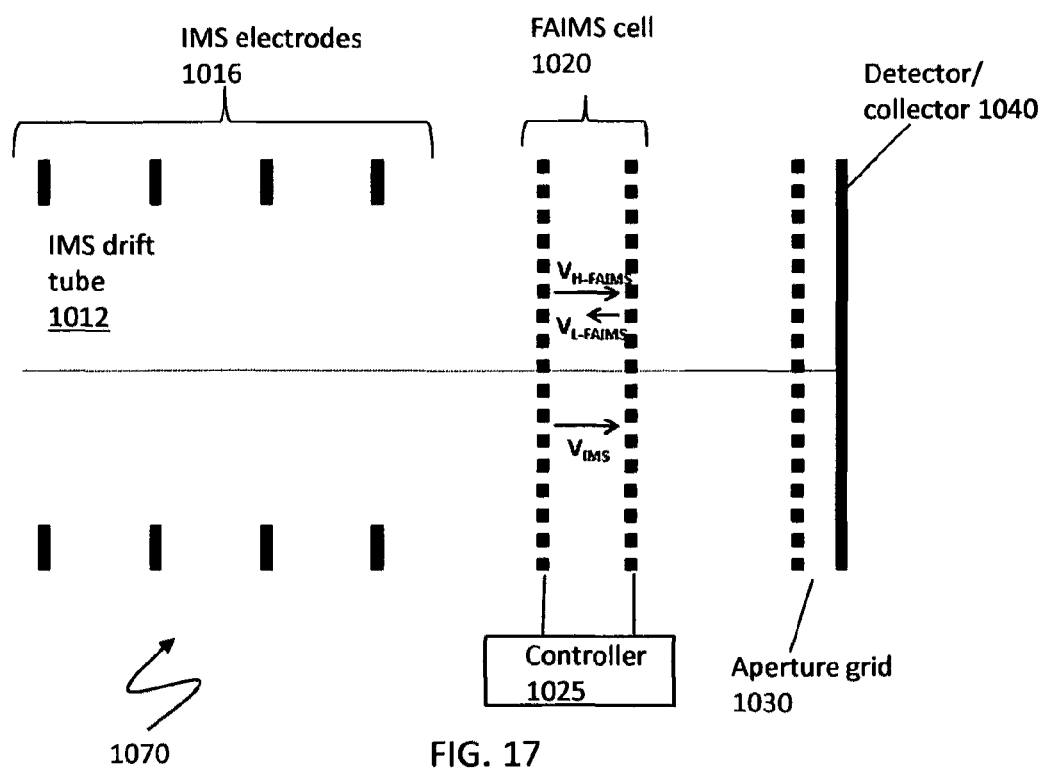
FIG. 17 is a schematic illustration showing ion velocities within the FAIMS cell according to an embodiment of the system described herein.

FIG. 17 is a schematic illustration 1070 identifying ion velocities within the FAIMS cell 1020 according to an embodiment of the system described herein. Ions are propelled through the IMS drift tube 1012 by IMS electrodes 1016 to the FAIMS cell 1020 embedded somewhere along the axis of the IMS drift tube 1012. Within the FAIMS cell 1020, the ions are subject to electrostatic forces due to the IMS field. $V_{ims}$ is the ion velocity due to the IMS field. A controller 1025 is shown that may control the field generated between the plates of the FAIMS device according to the high field asymmetric waveform operation of the system described herein. $V_{FAIMS}$ is the net velocity of the ions due to the asymmetric waveform. $V_{FAIMS}$ may be calculated according to Equation 4:

$$V_{FAIMS} = V_{H\text{-}FAIMS} - V_{L\text{-}FAIMS} = K_H E_H - K_L E_L \qquad \text{Eq. (4)}$$

where $V_{H\text{-}FAIMS}$ is the velocity and $K_H$ the mobility during the high field ($E_H$) and $V_{L\text{-}FAIMS}$ the velocity and $K_L$ the mobility during the low field ($E_L$).

Figure 18:
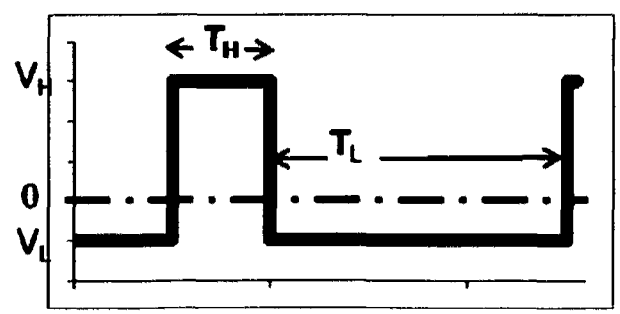
FIG. 18 is a plot showing parameters of an ideal asymmetric waveform in connection with an embodiment of the system described herein.

The flight time though the FAIMS cell $T_{cell}$ is governed by the IMS field as well as the oscillations due to the FAIMS field. $T_{cell}$ can be derived from the following:

$$1/T_{cell} = 1/T_{IMS} + E_H T_H (K_H - K_L)/W \cdot (T_H + T_L) \quad \text{Eq. (5)}$$

$$T_{IMS} = W/K \cdot E_{IMS} \quad \text{Eq. (6)}$$

where W is the width of the cell, K is the IMS mobility, $T_H$ and $T_L$ are the duration of the high and low fields within the asymmetric waveform (see FIG. 18).

FIG. 18 is a plot 1080 showing parameters of an asymmetric waveform that may be used in connection with an embodiment of the system described herein. $T_H$ and $T_L$ show the duration of the high and low fields within the asymmetric waveform. Depending on the polarity of the waveform and the polarity of the difference between the high field and low field mobilities, $T_{cell}$ is either shorter or longer than $T_{IMS}$. Assuming the analysis of negative ions and assuming a positive waveform (the high field segment is positive while the low field segment is negative), type A ions (larger mobility at higher fields) move slower through the cell while type C ions move faster through the cell causing a few ms shifts in the IMS spectrum (see FIG. 19). Other FAIMS parameters that affect the transit time in the cell include the high field $E_H$ and the duty cycle of the asymmetric waveform $T_H/(T_H + T_L)$.

Figure 19:
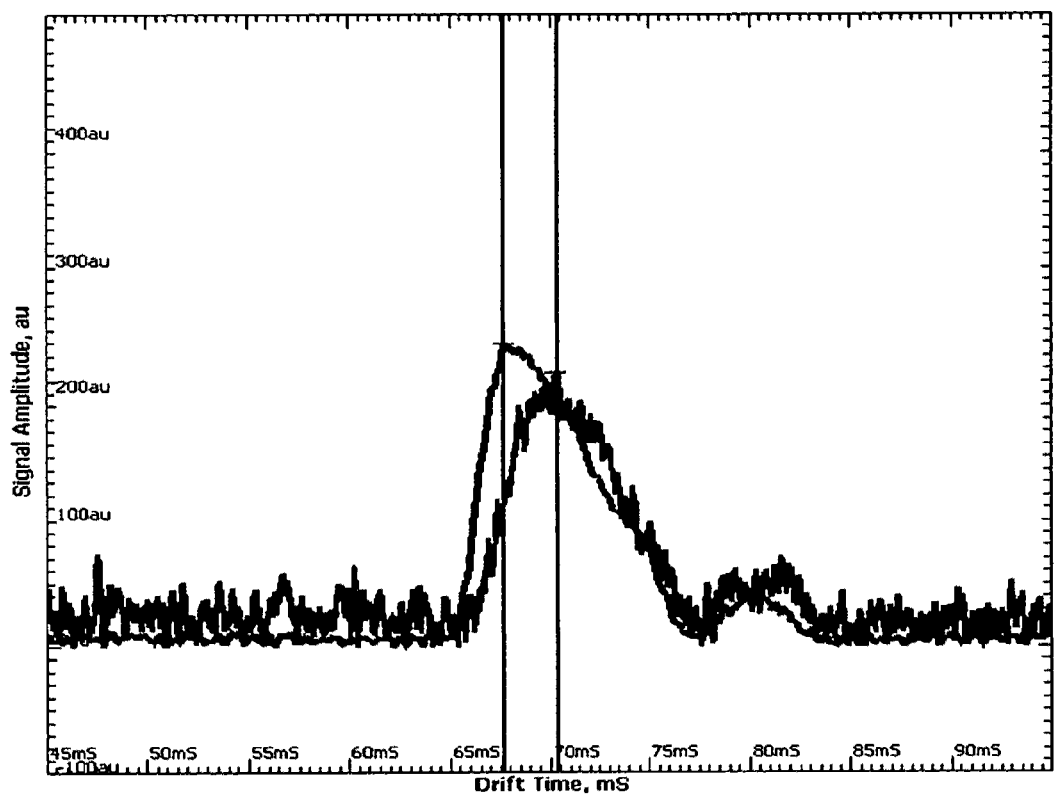
FIG. 19 is a plot of drift time (ms) along the x-axis and signal amplitude (au) along the y-axis that may be used in connection with an embodiment of the system described herein.

FIG. 19 is a plot 1090 of drift time (ms) along the x-axis and signal amplitude (au) along the y-axis that may be used in connection with an embodiment of the system described herein. The plot shows about a 2.75 ms shift to the right upon applying the high frequency dispersion voltage according to an embodiment of the system described herein. As discussed, by performing oscillations within the FAIMS cell, ions are either accelerated or decelerated depending on whether the high field mobility (KH) is higher (type A) or lower (type C). Upon applying the high frequency field shifts along the drift time axis of the IMS spectrum, of various amounts depending on the compounds, are observed including with the reactive ions. This represents an additional dimension for separation that combines low and high properties of the mobility of the species into the same spectrum. As illustrated and noted, assuming the analysis of negative ions and assuming a positive waveform (the high field segment is positive while the low field segment is negative), type A ions (larger mobility at higher fields) move slower through the cell while type C ions move faster through the cell causing a few ms (2.75, as shown) shift in the IMS spectrum.

Figure 20:
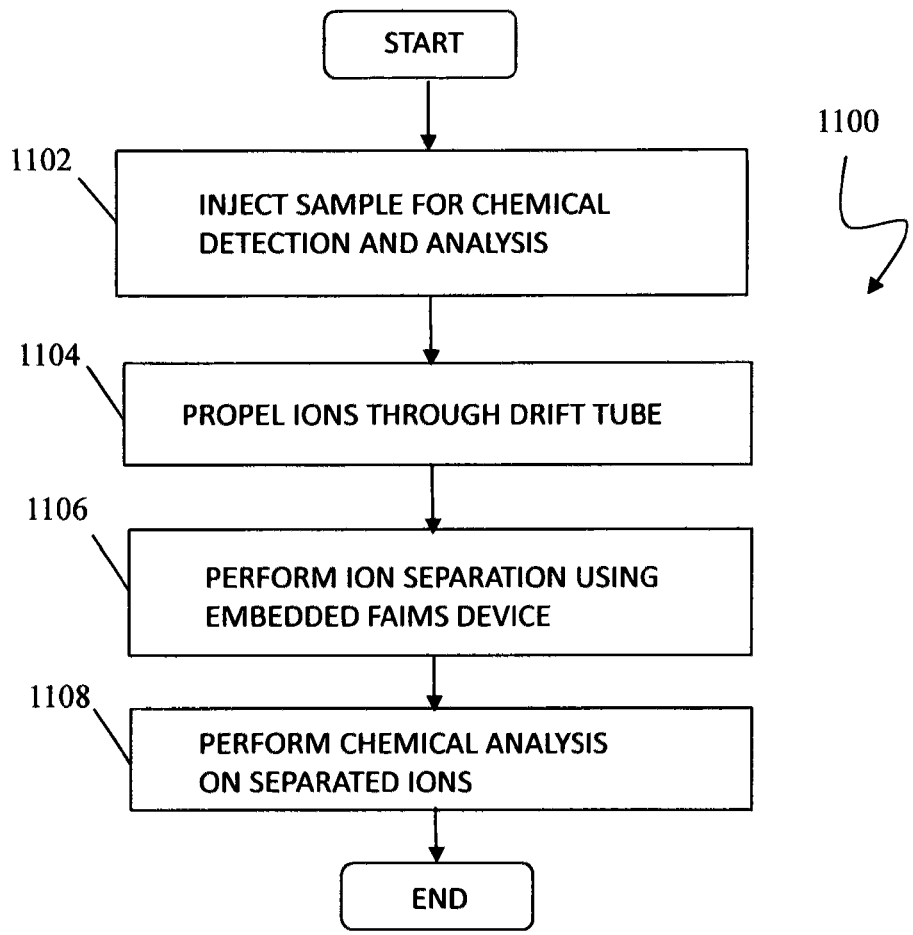
FIG. 20 is a flow diagram showing chemical analysis and detection processing steps using an embedded FAIMS device according to an embodiment of the system described herein.

FIG. 20 is a flow diagram 1100 showing chemical analysis and detection processing steps using an embedded FAIMS device according to an embodiment of the system described herein. At a step 1102, a sample gas on which chemical analysis and detection is to be performed is provided through a sample inlet to a IMS/FAIMS system according to that described herein. After the step 1102, processing proceeds to a step 1104 where ion mobility spectrometry processing is performed using the IMS device to ionize the sample and to propel the resulting ions through a drift tube. After the step 1104, processing proceeds to a step 1106 where at least some ions are separated according to operation of the embedded FAIMS device, as further discussed elsewhere herein, involving the use of oscillations of the ions and in which the direction of the generated oscillations is co-axial with the direction of the propelled ions through the drift tube. The oscillations cause a net change in velocity of at least some ions moving along the axial direction of the drift tube. As discussed elsewhere herein, depending on the nature of the mobility of the ions at high fields compared to that at low fields, the ions will either be accelerated or decelerated through the cell (and even including being stopped), thus causing the shift in their respective drift times that enables the desired ion separations for purposes of measurement. After the step 1106, processing proceeds to a step 1108 where chemical analysis is performed on the ions (ions of interest) that have been separated according to the system described herein. After the step 1108, processing is complete.

Figure 21:
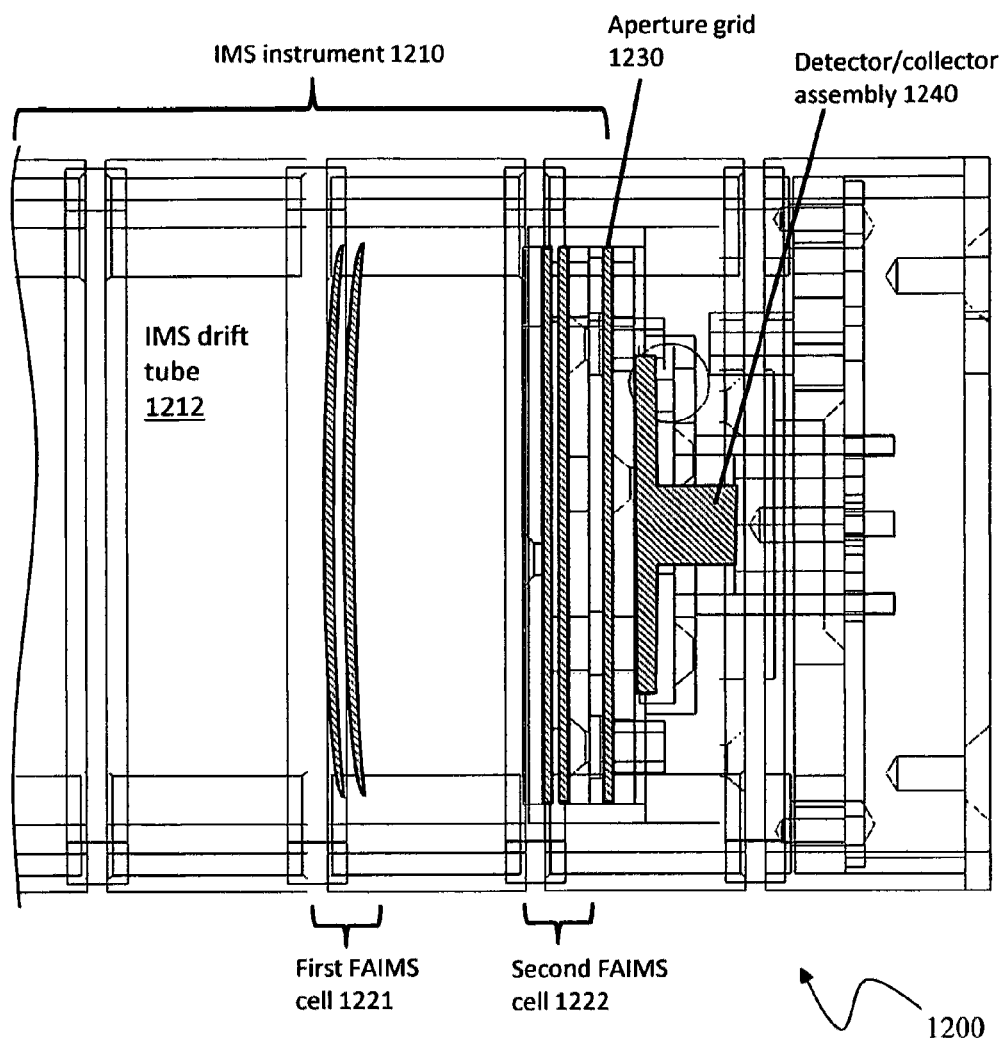
FIG. 21 is a schematic illustration of a chemical analysis and detection system having multiple FAIMS cells embedded in an IMS drift tube and including FAIMS cells having planar and non-planar geometries according to an embodiment of the system described herein.

FIG. 21 is a schematic illustration of a chemical analysis and detection system 1200 having multiple FAIMS cells 1221, 1222 embedded in an IMS drift tube 1212 of an IMS instrument 1210 according to an embodiment of the system described herein. As discussed elsewhere herein, the FAIMS cells 1221, 1222 may be embedded at any suitable location along the IMS drift tube 1212. The FAIMS cells 1221, 1222 are both embedded via insertion in front of the aperture grid 1230 and detector/collector assembly 1240. Although two FAIMS cells are illustrated, it is noted that more than two FAIMS cells may also be used in connection with the system described herein. In the illustrated example, the first FAIMS cell 1221 is shown having a non-planar geometry (e.g., crescent-shaped electrodes) and the second FAIMS cell 1222 is shown having a planar geometry (e.g., plate electrodes). By having multiple FAIMS cells 1221, 1222 the time shifts of ions moving through the IMS drift tube may be enhanced thereby further improving operation of the system to separate and detect desired ions of interest.

Various embodiments discussed herein may be combined with each other in appropriate combinations in connection with the system described herein. Additionally, in some instances, the order of steps in the flowcharts, flow diagrams and/or described flow processing may be modified, where appropriate. Further, various aspects of the system described herein may be implemented using software, hardware, a combination of software and hardware and/or other computer-implemented modules or devices having the described features and performing the described functions. Software implementations of the system described herein may include executable code that is stored in a computer readable medium and executed by one or more processors. The computer readable medium may include a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer readable medium or computer memory on which executable code may be stored and executed by a processor. The system described herein may be used in connection with any appropriate operating system.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A chemical detection and analysis system, comprising:
an ion mobility spectrometer (IMS) device having a drift tube that includes a first end with a sample inlet and a second end that is downstream from the first end, wherein ions from ionization of a sample input via the sample inlet are introduced into the drift tube, and wherein the drift tube includes IMS electrodes that electrostatically propel the ions through the drift tube in a direction along an axis of the drift tube; and a high field asymmetric waveform ion mobility spectrometer (FAIMS) device embedded along the axis of the drift tube of the IMS device, wherein the FAIMS device is field-driven, the electrodes of the drift tube of the IMS device electrostatically propelling the ions through the FAIMS device in the direction along the axis of the drift tube, and wherein the FAIMS device includes FAIMS electrodes that cause oscillations of the ions in the direction along the axis of the drift tube resulting in a net change in velocity of at least some of the ions that are being propelled by the IMS electrodes in the direction along the axis of the drift tube.

2. The chemical detection and analysis system according to claim 1, wherein the FAIMS device has a planar geometry.

3. The chemical detection and analysis system according to claim 1, wherein the FAIMS device has a non-planar geometry.

4. The chemical detection and analysis system according to claim 1, further comprising:
a collector that analyzes ions of interest from the FAIMS device;
an aperture grid that directs the ions of interest to the collector.

5. The chemical detection and analysis system according to claim 1, further comprising:
a controller that controls a field generated in the FAIMS device to cause the oscillations of the ions.

6. The chemical detection and analysis system according to claim 1, further comprising:
an ionization source that ionizes the sample and generates the ions introduced into the drift tube.

7. The chemical detection and analysis system according to claim 1, wherein the FAIMS device is a first FAIMS device, and wherein the system further comprises:
at least a second FAIMS device embedded along the axis of the drift tube of the IMS device.

8. A method for performing chemical detection and analysis, comprising:
ionizing a sample in an ion mobility spectrometer (IMS) device having a drift tube that includes a first end with a sample inlet and a second end that is downstream from the first end, wherein ions from the ionization of the sample are introduced into the drift tube, and wherein the drift tube includes IMS electrodes that electrostatically propel the ions through the drift tube in a direction along an axis of the drift tube; and
controlling a high field asymmetric waveform ion mobility spectrometer (FAIMS) device embedded along the axis of the drift tube of the IMS device, wherein the FAIMS device is field-driven, the electrodes of the drift tube of the IMS device electrostatically propelling the ions through the FAIMS device in the direction along the axis of the drift tube, and wherein the FAIMS device includes FAIMS electrodes that cause oscillations of the ions in the direction along the axis of the drift tube resulting in a net change in velocity of at least some of the ions that are being propelled by the IMS electrodes in the direction along the axis of the drift tube.

9. The method according to claim 8, further comprising:
directing the ions of interest to a collector and analyzing the ions of interest at the collector.

10. The method according to claim 8, further comprising:
controlling a field generated in the FAIMS device to cause the oscillations of the ions.

11. The method according to claim 8, wherein the FAIMS device is a first FAIMS device, and wherein the method further comprises:
controlling at least a second FAIMS device embedded along the axis of the drift tube of the IMS device, wherein the second FAIMS device is controlled to cause oscillations of the ions in the direction along the axis of the drift tube resulting in a net change in velocity of at least some of the ions moving in the direction along the axis of the drift tube.

12. A non-transitory computer readable medium method storing software for performing chemical detection and analysis, the software comprising:
executable code that controls ionizing of a sample in an ion mobility spectrometer (IMS) device having a drift tube that includes a first end with a sample inlet and a second end that is downstream from the first end, wherein ions from the ionization of the sample are introduced into the drift tube, and wherein the drift tube includes IMS electrodes that electrostatically propel the ions through the drift tube in a direction along an axis of the drift tube; and
executable code that controls a high field asymmetric waveform ion mobility spectrometer (FAIMS) device embedded along the axis of the drift tube of the IMS device, wherein the FAIMS device is field-driven, the electrodes of the drift tube of the IMS device electrostatically propelling the ions through the FAIMS device in the direction along the axis of the drift tube, and wherein the FAIMS device includes FAIMS electrodes that are controlled to cause oscillations of the ions in the direction along the axis of the drift tube resulting in a net change in velocity of at least some of the ions that are being propelled by the IMS electrodes in the direction along the axis of the drift tube.

13. The non-transitory computer readable medium according to claim 12, wherein the software further comprises:
executable code that controls directing of the ions of interest to a collector and analyzing the ions of interest at the collector.

14. The non-transitory computer readable medium according to claim 12, wherein the software further comprises:
executable code that controls a field generated in the FAIMS device to cause the oscillations of the ions.

15. The non-transitory computer readable medium according to claim 12, wherein the FAIMS device is a first FAIMS device, and wherein the method further comprises:
executable code that controls at least a second FAIMS device embedded along the axis of the drift tube of the IMS device, wherein the second FAIMS device is controlled to cause oscillations of the ions in the direction along the axis of the drift tube resulting in a net change in velocity of at least some of the ions moving in the direction along the axis of the drift tube.

* * * * *